United States Patent [19]
Nelson et al.

[11] Patent Number: 6,074,827
[45] Date of Patent: Jun. 13, 2000

[54] MICROFLUIDIC METHOD FOR NUCLEIC ACID PURIFICATION AND PROCESSING

[75] Inventors: Robert J. Nelson, Alameda; Herbert H. Hooper, Belmont; Alan K. Hauser, Palo Alto; Sharat Singh, San Jose; Stephen J. Williams, Burlingame; Alexander P. Sassi, Berkeley, all of Calif.

[73] Assignee: ACLARA Biosciences, Inc., Mountain View, Calif.

[21] Appl. No.: 09/018,918

[22] Filed: Feb. 5, 1998

Related U.S. Application Data

[63] Continuation-in-part of application No. 08/902,855, Dec. 2, 1997, which is a continuation-in-part of application No. 08/690,307, Jul. 30, 1996, Pat. No. 5,770,029.

[51] Int. Cl.[7] .............................. C12Q 1/68; C12P 19/34; C07H 21/00
[52] U.S. Cl. ........................... 435/6; 435/91.2; 435/7.93; 536/25.32; 536/25.4
[58] Field of Search ............................. 435/6, 91.2, 7.93; 536/25.32, 25.4

[56] References Cited

U.S. PATENT DOCUMENTS

| | | |
|---|---|---|
| 4,908,112 | 3/1990 | Pace ..................................... 204/299 R |
| 5,296,114 | 3/1994 | Manz ..................................... 204/180.1 |
| 5,726,026 | 3/1998 | Wilding et al. ......................... 435/7.21 |

*Primary Examiner*—Ardin H. Marschel
*Assistant Examiner*—Joyce Tung
*Attorney, Agent, or Firm*—Bertram I. Rowland; Rae-Venter Law Group, P.C.

[57] ABSTRACT

Integrated microfluidic devices comprising at least an enrichment channel and a main electrophoretic flowpath are provided. In the subject integrated devices, the enrichment channel and the main electrophoretic flowpath are positioned so that waste fluid flows away from said main electrophoretic flowpath through a discharge outlet. The subject devices find use in a variety of electrophoretic applications, including clinical assays, high throughput screening for genomics and pharmaceutical applications, point-or-care in vitro diagnostics, molecular genetic analysis and nucleic acid diagnostics, cell separations, and bioresearch generally.

18 Claims, 17 Drawing Sheets

5'-Dethiobiotin-Primer

MICROFLUIDIC METHOD FOR NUCLEIC ACID PURIFICATION AND PROCESSING

This application is a Continuation-in-Part of U.S. Ser. No. 08/902,855, filed Dec. 2, 1997, which is a Continuation-in-Part of U.S. Ser. No. 08/690,307, filed Jul. 30, 1996. Now U.S. Pat. No. 5,770,029.

BACKGROUND

This invention relates to microfluidics, and particularly to microchannel devices in which fluids are manipulated at least in part by application of electrical fields, Electrophoresis has become an indispensable tool of the biotechnology and other industries, as it is used extensively in a variety of applications, including the separation, identification and preparation of pure samples of nucleic acids, proteins, carbohydrates, the identification of a particular analyte in a complex mixture, and the like. Of increasing interest in the broader field of electrophoresis is capillary electrophoresis (CE), where particular entities or species are moved through a medium in an electrophoretic chamber of capillary dimensions under the influence of an applied electric field. Benefits of CE include rapid run times, high separation efficiency, small sample volumes, etc. Although CE was originally carried out in capillary tubes, of increasing interest is the practice of using microchannels or trenches of capillary dimension on a planar substrate, known as microchannel electrophoresis (MCE). CE and MCE are increasingly finding use in a number of different applications in both basic research and industrial processes, including analytical, biomedical, pharmaceutical, environmental, molecular, biological, food and clinical applications.

Despite the many advantages of CE and MCE, the potential benefits of these techniques have not yet been fully realized for a variety of reasons. Because of the nature of the electrophoretic chambers employed in CE and MCE, good results are not generally obtainable with samples having analyte concentrations of less than about $10^{-6}$ M. This lower analyte concentration detection limit has significantly limited the potential applications for CE and MCE. For example, CE and MCE have not found widespread use in clinical applications, where often an analyte of interest is present in femtomolar to nanomolar concentration in a complex sample, such as blood or urine.

In order to improve the detection limits of CE, different techniques have been developed, including improved sample injection procedures, such as analyte stacking (Beckers & Ackermans, "The Effect of Sample Stacking for High Performance Capillary Electrophoresis," J. Chromatogr. (1993) 629: 371–378), field amplification (Chien & Burgi, "Field Amplified Sample Injection in High-Performance Capillary Electrophoresis," J. Chromatogr. (1991) 559: 141–152), and transient isotachophoresis (Stegehuis et al, "Isotachophoresis as an On-Line Concentration Pretreatment Technique in Capillary Electrophoresis," J. Chromatogr. (1991) 538: 393–402), as well as improved sample detection procedures and "off-line" sample preparation procedures.

Another technique that has been developed to improve the detection limit achievable with CE has been to employ an analyte preconcentration device that is positioned directly upstream from the capillary, i.e., in an "on-line" or "single flow path" relationship. As used herein, the term "on-line" and "single flow path" are used to refer to the relationship where all of the fluid introduced into the analyte preconcentration component, i.e., the enriched fraction and the remaining waste fraction of the original sample volume, necessarily flows through the main electrophoretic portion of the device, i.e., the capillary tube comprising the separation medium. A review of the various configurations that have been employed is provided in Tomlinson et al., "Enhancement of Concentration Limits of Detection in CE and CE-MS: A Review of On-Line Sample Extraction, Cleanup, Analyte Preconcentration, and Microreactor Technology," J. Cap. Elec. (1995) 2: 247–266, and the figures provided therein.

Although this latter approach can provide improved results with regard to analyte detection limits, particularly with respect to the concentration limit of detection, it can have a deleterious impact on other aspects of CE, and thereby reduce the overall achievable performance. For example, analyte peak widths can be broader in on-line or single flow path devices comprising analyte preconcentrators.

Accordingly, there is continued interest in the development of improved CE devices capable of providing good results with samples having low concentrations of analyte, particularly analyte concentrations in the femtomolar to nanomolar range.

MCE devices are disclosed in U.S. Pat. No. 5,126,022; U.S. Pat. No. 5,296,114; U.S. Pat. No. 5,180,480; U.S. Pat. No. 5,132,012; and U.S. Pat. No. 4,908,112. Other references describing MCE devices include Harrison et al., "Micromachining a Miniaturized Capillary Electrophoresis-Based Chemical Analysis System on a Chip," Science (1992) 261: 895; Jacobsen et al., "Precolumn Reactions with Electrophoretic Analysis Integrated on a Microchip," Anal. Chem. (1994) 66: 2949; Effenhauser et al., "High-Speed Separation of Antisense Oligonucleotides on a Micromachined Capillary Electrophoresis Device," Anal. Chem. (1994) 66:2949; and Woolley & Mathies, "Ultra-High-Speed DNA Fragment Separations Using Capillary Array Electrophoresis Chips," P.N.A.S. USA (1994) 91:11348.

Patents disclosing devices and methods for the preconcentration of analyte in a sample "on-line" prior to CE include U.S. Pat. No. 5,202,010; U.S. Pat. No. 5,246,577 and U.S. Pat. No. 5,340,452. A review of various methods of analyte preconcentration employed in CE is provided in Tomlinson et al., "Enhancement of Concentration Limits of Detection in CE and CE-MS: A Review of On-Line Sample Extraction, Cleanup, Analyte Preconcentration, and Microreactor Technology," J. Cap. Elec. (1995) 2: 247–266.

SUMMARY OF THE INVENTION

Integrated electrophoretic microdevices comprising at least an enrichment channel and a main electrophoretic flowpath, as well as methods for their use in electrophoretic applications, are provided. The enrichment channel serves to enrich a particular fraction of a liquid sample for subsequent movement through the main electrophoretic flowpath. In the subject devices, the enrichment channel and electrophoretic flowpath are positioned such that waste fluid from the enrichment channel does not flow through the main electrophoretic flowpath, but instead flows through a discharge outlet. The subject devices find use in a variety of electrophoretic applications, where entities are moved through a medium in response to an applied electric field. The subject devices can be particularly useful in high throughput screening, for genomics and pharmaceutical applications such as gene discovery, drug discovery and development, and clinical development; for point-of-care in vitro diagnostics; for molecular genetic analysis and nucleic acid diagnostics; for cell separations including cell isolation and capture; and for bioresearch generally.

DETAILED DESCRIPTION

Figure 1:
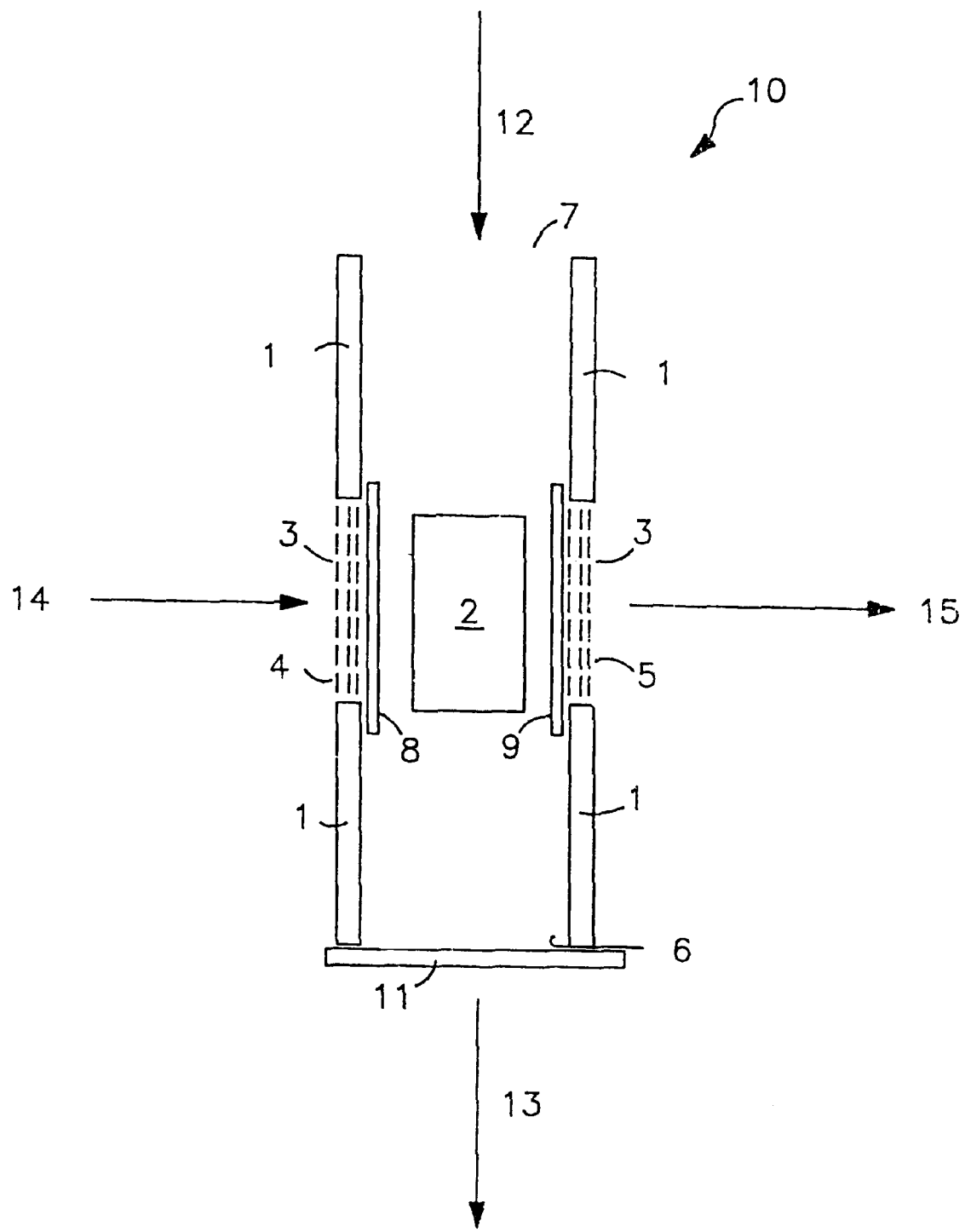
FIG. 1 provides a diagrammatic view of an enrichment channel for use in a device according to the subject invention.

Integrated electrophoretic microdevices comprising at least an enrichment channel and a main electrophoretic flowpath are provided. The enrichment channel serves to enrich a particular analyte comprising fraction of a liquid sample. The enrichment channel and main electrophoretic flowpath are positioned in the device so that waste fluid from the enrichment channel does not flow through the main electrophoretic channel, but instead flows away from the main electrophoretic flowpath through a discharge outlet. The subject devices may be used in a variety of electrophoretic applications, including clinical assay applications. In further describing the invention, the devices will first be described in general terms followed by a discussion of representative specific embodiments of the subject devices with reference to the figures.

The subject device is an integrated electrophoretic microdevice. By integrated is meant that all of the components of the device, e.g., the enrichment channel, the main electrophoretic flowpath, etc., are present in a single, compact, readily handled unit, such as a chip, disk or the like. As the devices are electrophoretic, they are useful in a wide variety of the applications in which entities, such as molecules, particles, cells and the like are moved through a medium under the influence of an applied electric field. Depending on the nature of the entities, e.g., whether or not they carry an electrical charge, as well as the surface chemistry of the electrophoretic chamber in which the electrophoresis is carried out, the entities may be moved through the medium under the direct influence of the applied electric field or as a result of bulk fluid flow through the pathway resulting from the application of the electric field, e.g., electroosmotic flow (EOF). The microdevices will comprise a microchannel as the main electrophoretic flowpath. By microchannel is meant that the electrophoretic chamber of the main electrophoretic flowpath in which the medium is present is a conduit, e.g., trench or channel, having a cross sectional area which provides for capillary flow through the chamber, where the chamber is present on a planar substrate, as will be described below in greater detail.

According to the invention the device includes an enrichment channel that includes a sample inlet and at least one fluid outlet, and contains an enrichment medium for enriching a particular fraction of a sample; optionally, the device further includes a second fluid outlet. The purpose of the enrichment channel is to process the initial sample to enrich for a particular fraction thereof, where the particular fraction being enriched includes the analyte or analytes of interest. The enrichment channel can thus serve to selectively separate the fraction containing the target analyte from the remaining components of the initial sample volume. The target-containing fraction may be retained within the enrichment channel, and the remainder flushed out from the channel for disposal or further treatment downstream; or, alternatively, selected components may be retained within the enrichment channel, and the target-containing fraction may be permitted to pass downstream for further processing.

Depending on the particular application in which the device is employed, the enrichment channel can provide for a number of different functions. The enrichment channel can serve to place the analyte of interest into a smaller volume than the initial sample volume, i.e., it can serve as an analyte concentrator. Furthermore, it can serve to prevent potentially interfering sample components from entering and flowing through the main electrophoretic flowpath, i.e., it can serve as a sample "clean-up" means. In addition, the enrichment channel may serve as a microreactor for preparative processes on target analyte present in a fluid sample, such as chemical, immunological, and enzymatic processes, e.g., labeling, protein digestion, DNA digestion or fragmentation, DNA synthesis, and the like.

The enrichment channel may be present in the device in a variety of configurations, depending on the particular enrichment medium housed therein. The internal volume of the channel will usually range from about 1 pl to 1 $\mu$l, usually from about 1 pl to 100 nl, where the length of the channel will generally range from about 1 $\mu$m to 5 mm, usually 10 $\mu$m to 1 mm, and the cross-sectional dimensions (e.g., width, height) will range from about 1 $\mu$m to 200 $\mu$m, usually from about 10 $\mu$m to 100 $\mu$m. The cross-sectional shape of the channel may be circular, ellipsoid, rectangular, trapezoidal, square, or other convenient configuration.

A variety of different enrichment media may be present in the enrichment channel. Representative enrichment medium or means include those means described in the analyte preconcentration devices disclosed in U.S. Pat. No. 5,202,010; U.S. Pat. No. 5,246,577 and U.S. Pat. No. 5,340,452, as well as Tomlinson et al., supra, the disclosures of which are herein incorporated by reference. Specific enrichment means known in the art which may be adaptable for use in the subject integrated microchannel electrophoretic devices include: those employed in protein preconcentration devices described in Kasicka & Prusik, "Isotachophoretic Electrodesorption of Proteins from an Affinity Adsorbent on a Microscale," J. Chromatogr. (1983) 273:117128; capillary bundles comprising an affinity adsorbent as described in U.S. Pat. No. 5,202,101 and WO 93/05390; octadodecylsilane coated solid phases as described in Cai & El Rassi, "On-Line Preconcentration of Triazine Herbicides with Tandem Octadecyl Capillaries-Capillary Zone Electrophoresis," J. Liq. Chromatogr. (1992) 15:1179–1192; solid phases coated with a metal chelating layer as described in Cai & El Rassi, "Selective On-Line Preconcentration of Proteins by Tandem Metal Chelate Capillaries-Capillary Zone Electrophoresis," J. Liq. Chromatogr. (1993) 16:2007–2024; reversed-phase HPLC solid packing materials as described in U.S. Pat. No. 5,246,577), Protein G coated solid phases as described in Cole & Kennedy, "Selective Preconcentration for Capillary Zone Electrophoresis Using Protein G Immunoaffinity Capillary Chromatography," Electrophoresis (1995) 16:549–556; meltable agarose gels as described in U.S. Pat. No. 5,423,966; affinity adsorbent materials as described in Guzman, "Biomedical Applications of On-Line Preconcentration - Capillary Electrophoresis Using an Analyte Concentrator: Investigation of Design Options," J. Liq. Chromatogr. (1995) 18:3751–3568); and solid phase reactor materials as described in U.S. Pat. No. 5,318,680. The disclosures of each of the above-referenced patents and other publications are hereby incorporated by reference herein.

One class of enrichment media or materials that may find use as enrichment media are chromatographic media or materials, particularly sorptive phase materials. Such materials include: reverse phase materials, e.g., C8 or C18 compound coated particles; ion-exchange materials; affinity chromatographic materials in which a binding member is covalently bound to an insoluble matrix, where the binding member may group specific, e.g., a lectin, enzyme cofactor, Protein A and the like, or substance specific, e.g., antibody or binding fragment thereof, antigen for a particular antibody of interest, oligonucleotide and the like, where the insoluble matrix to which the binding member is bound may be particles, such as porous glass, polymeric beads, magnetic beads, networks of glass strands or filaments, a plurality of narrow rods or capillaries, the wall of the channel and the like. Depending on the nature of the chromatographic material employed as the enrichment means, it may be necessary to employ a retention means to keep the chromatographic material in the enrichment channel. Conveniently, glass frits or plugs of agarose gel may be employed to cover the fluid outlets or inlets of the chamber, where the frits or plugs allow for fluid flow but not for particle or other insoluble matrix flow out of the enrichment channel. In embodiments where the enrichment means is a chromatographic material, typically sample will be introduced into, and allowed to flow through, the enrichment channel. As the sample flows through the enrichment channel, the analyte comprising fraction will be retained in the enrichment channel by the chromatographic material and the remaining waste portion of the sample will flow out of the channel through the waste outlet.

In embodiments where the enrichment means is a bed of polymeric beads or paramagnetic beads or particles, the beads may be coated with antibodies or other target-specific affinity binding moiety, including: affinity purified monoclonal antibodies to any of a variety of mammalian cell markers, particularly human cell markers, including markers for T cells, T cell subsets, B cells, monocytes, stem cells, myeloid cells, leukocytes, and HLA Class II positive cells; secondary antibodies to any of a variety of rodent cell markers, particularly mouse, rat or rabbit immunoglobulins, for isolation of B cells, T cells, and T cell subsets; uncoated or tosylactivated form for custom coating with any given biomolecule; and streptavidin-coated for use with biotinylated antibodies. Paramagnetic beads or particles may be retained in the enrichment channel by application of a magnetic field.

Alternatively, or in addition to solid phase materials such as coated particles or other insoluble matrices as the enrichment means, one may employ a coated and/or impregnated membrane which provides for selective retention of the analyte comprising fraction of the sample while allowing the remainder of the sample to flow through the membrane and out of the enrichment means through the waste outlet. A variety of hydrophilic, hydrophobic and ion-exchange membranes have been developed for use in solid phase extraction which may find use in the subject invention. See, for example, Tomlinson et al, "Novel Modifications and Clinical Applications of Preconcentration-Capillary Electrophoresis-Mass Spectrometry," J. Cap. Elect. (1995) 2:97–104; and Tomlinson et al, "Improved On-line Membrane Preconcentration-Capillary Electrophoresis (mPC-CE)," J. High Res. Chromatogr. (1995) 18:381–3.

Alternatively or additionally, the enrichment channel or the enrichment medium can include a porous membrane or filter. Suitable materials for capturing genomic DNAs and viral nucleic acids include those marketed by QIAGEN under the name QIAmp, for analysis of blood, tissues, and viral RNAs; and suitable materials for capturing DNAs from plant cells and tissues include those marketed by QIAGEN under the name DNeasy.

Depending on the configuration of the device, the sample can be caused to flow through the enrichment channel by any of a number of different means, and combinations of means. In some device configurations, it may be sufficient to allow the sample to flow through the device as a result of gravity forces on the sample; in some configurations, the device may be spun about a selected axis to impose a centrifugal force in a desired direction. In other embodiments, active pumping means may be employed to move sample through the enrichment channel and enrichment means housed therein. In other embodiments, magnetic forces may be applied to move the sample or to capture or immobilize a paramagnetic bead-target complex during wash and elution steps. In yet other embodiments of the subject invention, electrodes may be employed to apply an electric field which causes fluid to move through the enrichment channel. An elution liquid will then be caused to flow through the enrichment medium to release the enriched sample fraction from the material and carry it to the main electrophoretic flowpath. Generally, an applied electric field will be employed to move the elution liquid through the enrichment channel.

Electrophoretic gel media may also be employed as enrichment means in the subject applications. Gel media providing for a diversity of different sieving capabilities are known. By varying the pore size of the media, employing two or more gel media of different porosity, and/or providing for a pore size gradient and selecting the appropriate relationship between the enrichment channel and the main electrophoretic flowpath, one can ensure that only the analyte comprising fraction of interest of the initial sample enters the main electrophoretic flowpath. For example, one could have a device comprising an enrichment channel that intersects the main electrophoretic channel, where the enrichment channel comprises, in the direction of sample flow, a stacking gel of large porosity and a second gel of fine porosity, where the boundary between the gels occurs in the intersection of the enrichment channel and the main electrophoretic flowpath. In this embodiment, after sample is introduced into the stacking gel and an electric field applied to the gels in the enrichment channel, the sample components move through the stacking gel and condense into a narrow band at the gel interface in the intersection of the enrichment channel and main electrophoretic flowpath. A second electric field can then be applied to the main electrophoretic flowpath so that the narrow band of the enriched sample fraction moves into and through the main electrophoretic flowpath. Alternatively, the enrichment channel could comprise a gel of gradient porosity. In this embodiment, when the band(s) of interest reaches the intersection of the enrichment channel and electrophoretic flowpath, the band(s) of interest can then be moved into and along the main electrophoretic flowpath.

Enrichment media that can be particularly useful for enrichment and/or purification of nucleic acids include sequence specific capture media as well as generic capture media. Generic capture media include, for example: ion exchange and silica resins or membranes which nonspecifically bind nucleic acids, and which can be expected to retain substantially all the DNA in a sample; immobilized single-stranded DNA binding protein (SSB Protein), which can be expected to bind substantially all single-stranded DNA in a sample; poly-dT modified beads, which can be expected to bind substantially all the mRNA in a sample. Sequence specific capture media include beads, membranes or surfaces on which are immobilized any of a variety of capture molecules such as, for example: oligonucleotide probes, which can be expected to bind nucleic acids having complementary sequences in the sample; streptaviden, which can be expected to bind solution phase biotinylated probes which have hybridized with complementary sequences in the sample. Suitable beads for immobilization of capture molecules include chemically or physically crosslinked gels and porous or non-porous resins such as polymeric or silica-based resins.

Suitable capture media for proteins include the following. Suitable capture media for proteins include: ion exchange resins, including anion (e.g., DEAE) and cation exchange; hydrophobic interaction compounds (e.g., C4, C8 and C18 compounds); sulfhydryls; heparins; inherently active surfaces (e.g., plastics, nitrocellulose blotting papers); activated plastic surfaces; aromatic dyes such as Cibacron blue, Remazol orange, and Procion red. For carbohydrate moieties of proteins, lectins, immobilized hydrophobic octyl and phenylalkane derivatives can be suitable. For enzymes, analogs of a specific enzyme substrate-product transition-state intermediate can be suitable; for kinases, calmodulin can be suitable. Suitable capture media for receptors include receptor ligand affinity compounds.

As mentioned above, the enrichment channel will comprise at least one inlet and at least one outlet. Of course, where there is a single inlet, the inlet must serve to admit sample to the enrichment channel at an enrichment phase of the process, and to admit an elution medium during an elution phase of the process. And where there is a single outlet, the outlet must serve to discharge the portion of the sample that has been depleted of the fraction retained by the enrichment media, and to pass to the main electrophoretic microchannel the enriched fraction during the elution phase. Depending on the particular enrichment means housed in the enrichment channel, as well as the particular device configuration, the enrichment channel may have more than one fluid inlet, serving as, e.g., sample inlet and elution buffer inlet; or the enrichment channel may have more than one outlet, serving as, e.g., waste outlet and enriched fraction fluid outlet. Where the enrichment channel is in direct fluid communication with the main electrophoretic channel, i.e., the enrichment channel and main electrophoretic flowpath are joined so that fluid flows from the enrichment channel immediately into the main electrophoretic flowpath, the enrichment channel will comprise, in addition to the waste outlet, an enriched fraction fluid outlet through which the enriched fraction of the sample flows into the main electrophoretic flowpath. When convenient, e.g., for the introduction of wash and/or elution solvent into the enrichment channel, one or more additional fluid inlets may be provided to conduct such solvents into the enrichment channel from fluid reservoirs. To control bulk fluid flow through the enrichment channel, e.g., to prevent waste sample from flowing into the main electrophoretic flowpath, fluid control means, e.g., valves, membranes, etc., may be associated with each of the inlets and outlets. Where desirable for moving fluid and entities through the enrichment channel, e.g., sample, elution buffer, reagents, reactants, wash or rinse solutions, etc., electrodes may be provided capable of applying an electric field to the material and fluid present in the enrichment channel.

The next component of the subject devices is the main electrophoretic flowpath. The main electrophoretic flowpath may have a variety of configurations, including tube-like, trench-like or other convenient configuration, where the cross-sectional shape of the flowpath may be circular, ellipsoid, square, rectangular, triangular and the like so that it forms a microchannel on the surface of the planar substrate in which it is present. The microchannel will have cross-sectional area which provides for capillary fluid flow through the microchannel, where at least one of the cross-sectional dimensions, e.g., width, height, diameter, will be at least about 1 µm, usually at least about 10 µm, but will not exceed about 200 µm, and will usually not exceed about 100 µm. Depending on the particular nature of the integrated device, the main electrophoretic flowpath may be straight, curved or another convenient configuration on the surface of the planar substrate.

The main electrophoretic flowpath, as well as any additional electrophoretic flowpaths, will have associated with it at least one pair of electrodes for applying an electric field to the medium present in the flowpath. Where a single pair of electrodes is employed, typically one member of the pair will be present at each end of the pathway. Where convenient, a plurality of electrodes may be associated with the electrophoretic flowpath, as described in U.S. Pat. No. 5,126,022, the disclosure of which is herein incorporated by reference, where the plurality of electrodes can provide for precise movement of entities along the electrophoretic flowpath. The electrodes employed in the subject device may be any convenient type capable of applying an appropriate electric field to the medium present in the electrophoretic flowpath with which they are associated.

Critical to the subject invention is that the enrichment channel and the main electrophoretic flowpath are positioned in the device so that substantially only the enriched fraction of the sample flows through the main electrophoretic flowpath. To this end, the device will further comprise a discharge outlet for discharging a portion of sample other than the enriched fraction, e.g., the waste portion, away from the main electrophoretic flowpath. Thus, where the enrichment channel is in direct fluid communication with the main electrophoretic flowpath, the waste fluid flowpath through the enrichment channel will be in an intersecting relationship with the main electrophoretic flowpath. In other embodiments of the subject invention where the enrichment channel and main electrophoretic flowpath are connected by a second electrophoretic flowpath so that they are in indirect fluid communication, the waste flowpath through the enrichment channel does not necessarily have to be in an intersecting relationship with the main electrophoretic flowpath; the waste flowpath and main electrophoretic flowpath could be parallel to one another.

The subject devices will also comprise a means for transferring the enriched fraction from the enrichment channel to the main electrophoretic flowpath. Depending on the particular device configuration, the enriched fraction transfer means can be an enriched fraction fluid outlet, a secondary electrophoretic pathway, or other suitable transfer means. By having a second electrophoretic flowpath in addition to the main electrophoretic flowpath, the possibility exists to employ the second electrophoretic flowpath as a conduit for the enriched sample fraction from the enrichment channel to the main electrophoretic flowpath. In those embodiments where the waste outlet is the sole fluid outlet, the presence of a secondary electrophoretic flowpath will be essential, such that the enrichment channel and the main electrophoretic flowpath are in indirect fluid communication.

In addition to the main and any secondary electrophoretic flowpath serving as an enriched sample transfer means, the subject devices may further comprise one or more additional electrophoretic flowpaths, which may or may not be of capillary dimension and may serve a variety of purposes. With devices comprising a plurality of electrophoretic flowpaths, a variety of configurations are possible, such as a branched configuration in which a plurality of electrophoretic flowpaths are in fluid communication with the main electrophoretic flowpath. See U.S. Pat. No. 5,126,022, the disclosure of which is herein incorporated by reference.

The main electrophoretic flowpath and/or any secondary electrophoretic flowpaths present in the device may optionally comprise, and usually will comprise, fluid reservoirs at one or both termini, i.e., either end, of the flowpaths. Where reservoirs are provided, they may serve a variety of purposes, such as a means for introducing buffer, elution solvent, reagent, rinse and wash solutions, and the like into the main electrophoretic flowpath, receiving waste fluid from the electrophoretic flowpath, and the like.

Another optional component that may be present in the subject devices is a waste fluid reservoir for receiving and storing the waste portion of the initial sample volume from the enrichment channel, where the waste reservoir will be in fluid communication with the discharge outlet. Depending on the particular device configuration, the discharge outlet may be the same as, or distinct from, the waste outlet, and may open into a waste reservoir or provide an outlet from the device. The waste reservoir may be present in the device as a channel, compartment, or other convenient configuration which does not interfere with the other components of the device.

The subject device may also optionally comprise an interface means for assisting in the introduction of sample into the sample preparation means. For example, where the sample is to be introduced by syringe into the device, the device may comprise a syringe interface which serves as a guide for the syringe needle into the device, as a seal, and the like.

Depending on the particular configuration and the nature of the materials from which the device is fabricated, at least in association with the main electrophoretic flowpath will be a detection region for detecting the presence of a particular species in the medium contained in the electrophoretic flowpath. At least one region of the main electrophoretic flowpath in the detection region will be fabricated from a material that is optically transparent, generally allowing light of wavelengths ranging from 180 to 1500 nm, usually 220 to 800 nm, more usually 250 to 800 nm, to have low transmission losses. Suitable materials include fused silica, plastics, quartz glass, and the like.

The integrated device may have any convenient configuration capable of comprising the enrichment channel and main electrophoretic flowpath, as well as any additional components. Because the devices are microchannel electrophoretic devices, the electrophoretic flowpaths will be present on the surface of a planar substrate, where the substrate will usually, though not necessarily, be covered with a planar cover plate to seal the microchannels present on the surface from the environment. Generally, the devices will be small, having a longest dimension in the surface plane of no more than about 200 mm, usually no more than about 100 mm so that the devices are readily handled and manipulated. As discussed above, the devices may have a variety of configurations, including parallelepiped, e.g., credit card or chip like, disk like, syringe like or any other compact, convenient configuration.

The subject devices may be fabricated from a wide variety of materials, including glass, fused silica, acrylics, thermoplastics, and the like. The various components of the integrated device may be fabricated from the same or different materials, depending on the particular use of the device, the economic concerns, solvent compatibility, optical clarity, color, mechanical strength, and the like. For example, both the planar substrate comprising the microchannel electrophoretic flowpaths and the cover plate may be fabricated from the same material, e.g., polymethylmethacrylate (PMMA), or different materials, e.g., a substrate of PMMA and a cover plate of glass. For applications where it is desired to have a disposable integrated device, due to ease of manufacture and cost of materials, the device will typically be fabricated from a plastic. For ease of detection and fabrication, the entire device may be fabricated from a plastic material that is optically transparent, as that term is defined above. Also of interest in certain applications are plastics having low surface charge under conditions of electrophoresis. Particular plastics finding use include polymethylmethacrylate, polycarbonate, polyethylene terepthalate, polystyrene or styrene copolymers, and the like.

The devices may be fabricated using any convenient means, including conventional molding and casting techniques. For example, with devices prepared from a plastic material, a silica mold master which is a negative for the channel structure in the planar substrate of the device can be prepared by etching or laser micromachining. In addition to having a raised ridge which will form the channel in the substrate, the silica mold may have a raised area which will provide for a cavity into the planar substrate for housing of the enrichment channel. Next, a polymer precursor formulation can be thermally cured or photopolymerized between the silica master and support planar plate, such as a glass plate. Where convenient, the procedures described in U.S. Pat. No. 5,110,514, the disclosure of which is herein incorporated by reference, may be employed. After the planar substrate has been fabricated, the enrichment channel may be placed into the cavity in the planar substrate and electrodes introduced where desired. Finally, a cover plate may be placed over, and sealed to, the surface of the substrate, thereby forming an integrated device. The cover plate may be sealed to the substrate using any convenient means, including ultrasonic welding, adhesives, etc.

Generally, prior to using the subject device, a suitable first or electrophoretic medium will be introduced into the electrophoretic flowpaths or microchannels of the device, where the first medium will be different from the enrichment medium present in the enrichment channel. Electrophoretic media is used herein to refer to any medium to which an electric field is applied to move species through the medium. The electrophoretic media can be conveniently introduced through the reservoirs present at the termini of the electrophoretic flowpaths or directly into the channels or chambers of the electrophoretic flowpaths prior to sealing of the cover plate to the substrate. Any convenient electrophoretic medium may be employed. Electrophoretic media suitable for use, depending on the particular application, include buffers, crosslinked and uncrosslinked polymeric media, organic solvents, detergents, and the like, as disclosed in Barron & Blanch, "DNA Separations by Slab Gel and Capillary Electrophoresis: Theory and Practice," Separation and Purification Methods (1995) 24:1–118, as well as in U.S. patent applications Ser. Nos. 08/636,599 and 08/589,150, and U.S. Pat. No. 5,569,314 the disclosures of which are herein incorporated by reference. Of particular interest as electrophoretic media are cellulose derivatives, polyacrylamides, polyvinyl alcohols, polyethylene oxides, and the like.

The subject invention will now be further described in terms of the figures. FIG. 1 provides a diagrammatic view of an enrichment channel which may find use in the devices of the subject invention. Enrichment channel 10 comprises side walls 1 which enclose reverse phase C18 material 2. Channel 10 further comprise fluid inlets 7 and 4 and fluid outlets 5 and 6. For controlling fluid flow through the channel inlets and outlets, valves 8, 9 and 11 are provided. Glass frits 3 allow for fluid flow through inlet 4 and outlet 5 but restrain reverse phase material 2 in the channel. In using this enrichment channel, sample is introduced through sample inlet 7 in the direction of flowpath 12. As sample moves through channel 10, the analyte comprising fraction is retained on reverse phase material 2 while the remaining waste fraction of the sample flows out waste outlet 6 along flowpath 13. Valves 8 and 9 are closed to prevent sample from flowing or "bleeding" out inlet 4 or outlet 5. After the sample has flowed through channel 10, valve 11 is shut and valves 8 and 9 are opened. Elution buffer is then introduced into channel 10 through glass frit 3 and inlet 4 in the direction of flowpath 14. As elution buffer moves through material 2, the retained fraction of the sample is released and carried with the elution buffer out enriched fraction outlet 5 through frit 3 along flowpath 15.

Figure 2:
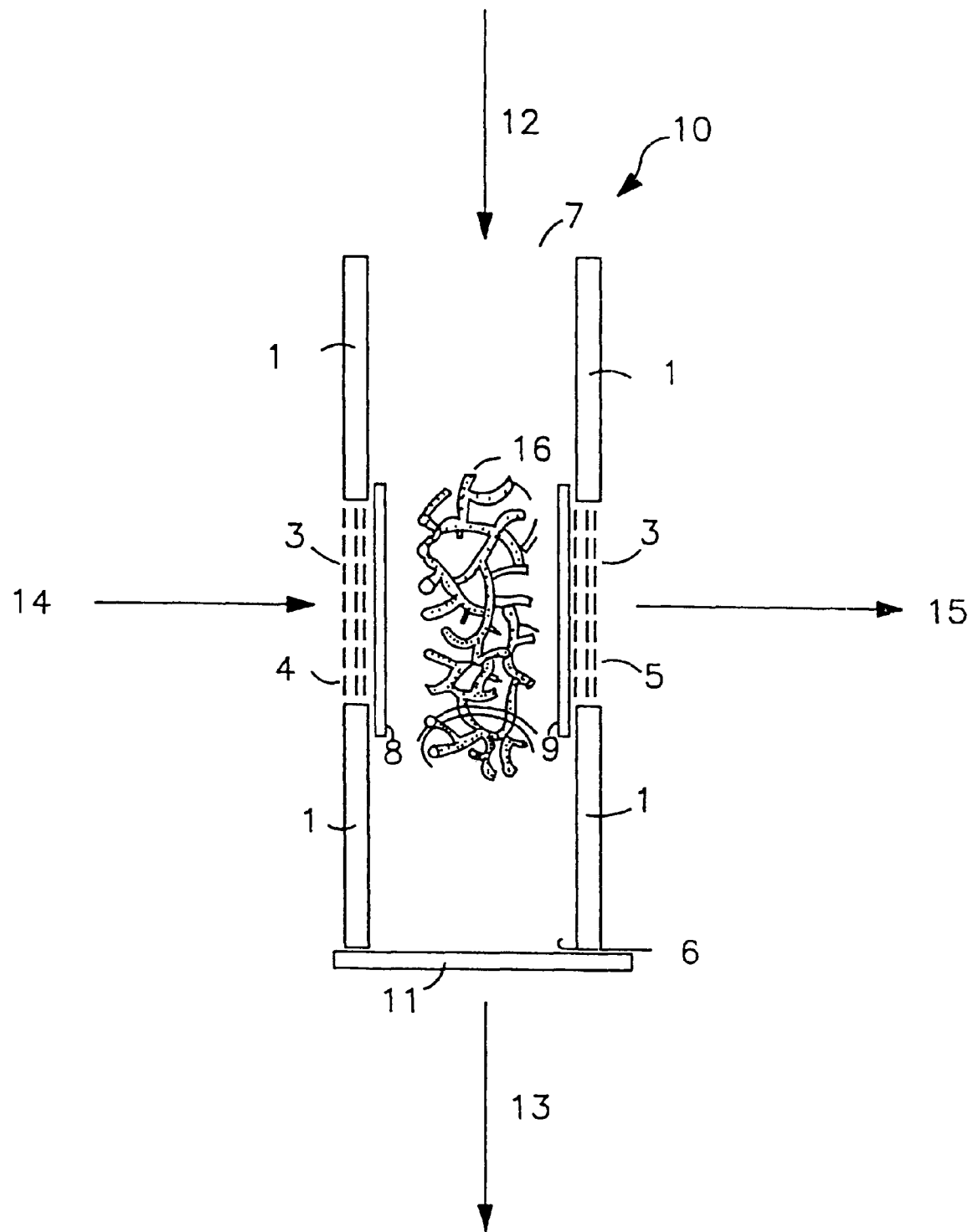
FIG. 2 provides a diagrammatic view of an alternative embodiment of an enrichment channel also suitable for use in the subject device.

In FIG. 2, the same enrichment channel as shown in FIG. 1 is depicted with the exception that reverse phase material 2 is replaced by a network of crosslinked glass filaments 16 to which binding pair member is covalently bound.

Figure 3A:
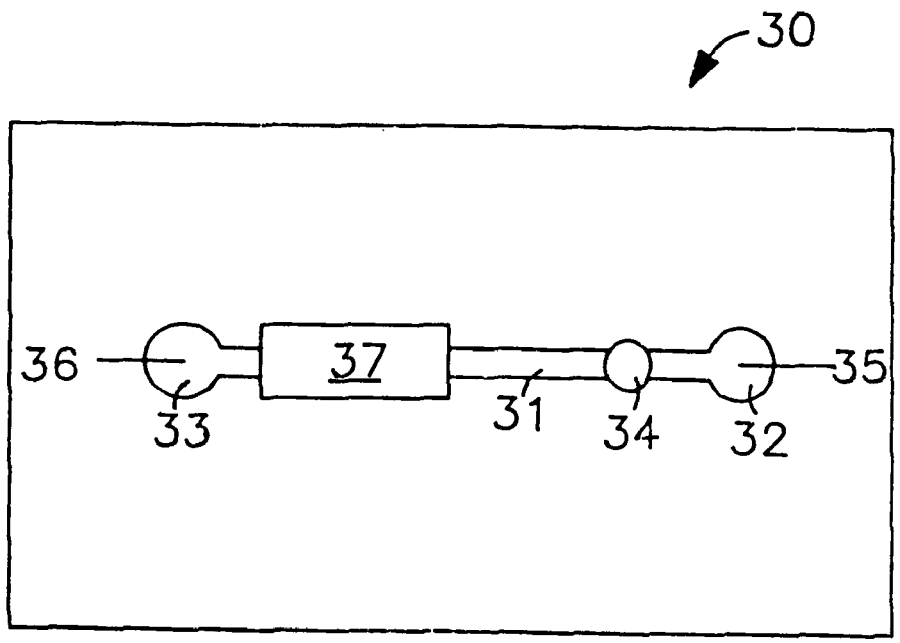
FIG. 3A provides a top diagrammatic view of a device according to the subject invention.

FIG. 3A provides a diagrammatic top view of a credit card shaped (parallelepiped) device according to the subject invention. Device 30 comprises main electrophoretic flowpath 31 having reservoir 32 at a first end and reservoir 33 at a second end. In direct fluid communication with main electrophoretic flowpath 31 is enrichment channel 34 (seen from overhead). Electrodes 35 and 36 are provided for applying an electric field to the medium present in electrophoretic flowpath 31. Detection region 37 is positioned over electrophoretic flowpath 31 for viewing analyte present in the medium comprised in the flowpath. A detection region can also be provided over the enrichment channel 34. Although the device shown in FIG. 3A comprises a single enrichment channel, additional enrichment channels could be provided in the flowpath, including in the detection region.

Figure 3B:
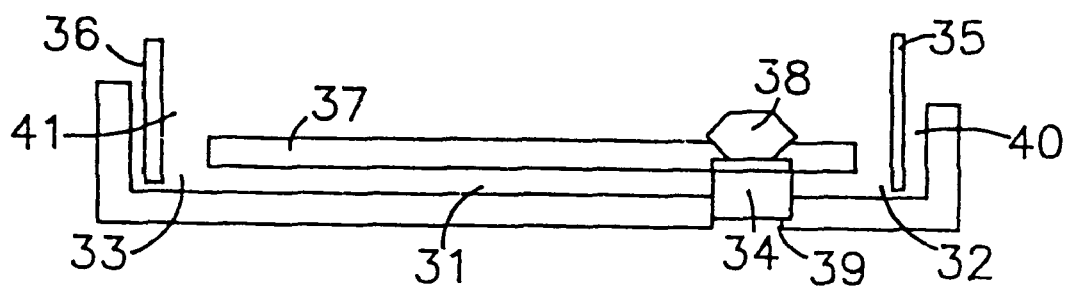
FIG. 3B provides a side view of the device of FIG. 3A.

FIG. 3B provides a diagrammatic side view of the device depicted in FIG. 3A. In using this embodiment of the subject invention, sample is introduced through syringe interface 38 into enrichment channel 34, where the analyte comprising fraction of the sample is retained as the waste fraction flows out of the enrichment channel 34 through discharge outlet 39 and out of the device. Elution buffer is then introduced into reservoir 32 through port 40. An electric field is then applied between electrodes 35 and 36 causing elution buffer to migrate from reservoir 32 through enrichment channel 34 and along electrophoretic flowpath 31 to reservoir 33. As the elution buffer moves through enrichment channel 34, it releases the retained analyte comprising fraction of the initial sample volume and carries it into electrophoretic flowpath 31.

Figure 4:
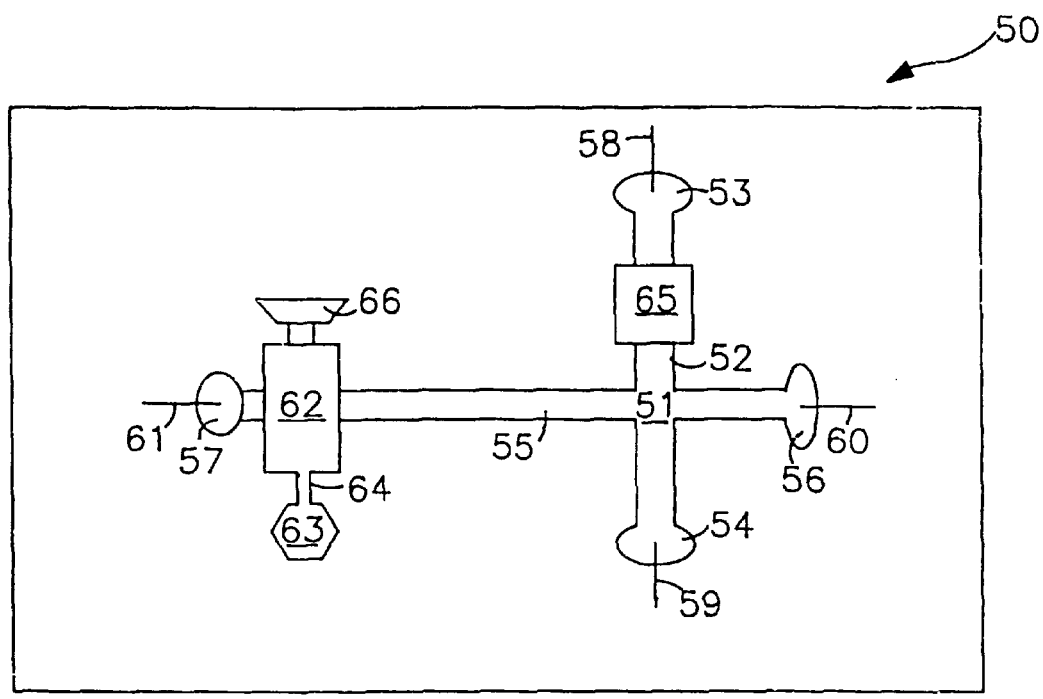
FIG. 4 provides a diagrammatic top view of another embodiment of the subject invention.

FIG. 4 shows a diagrammatic view of an embodiment of the subject invention in which the enrichment channel 62 is separated from main electrophoretic flowpath 52 by secondary electrophoretic flowpath 55. With device 50, sample is introduced into enrichment channel 62 through syringe interface 66. As sample flows through enrichment channel 62, waste sample flows through discharge outlet 64 into waste reservoir 63. An electric field is then applied between electrodes 61 and 60 causing elution buffer present in reservoir 57 to move through enrichment channel 62, resulting in the release of analyte. Analyte is then carried along secondary electrophoretic flowpath 55 along with the elution buffer. When analyte reaches intersection 51, the electric field between electrodes 60 and 61 is replaced by an electric field between electrodes 59 and 58. In this and other analogous embodiments of the subject invention, the time at which analyte reaches intersection 51 may be determined by detecting the presence of analyte in the intersection or by empirically determining the time at which the analyte should reach the intersection, based on the particular nature of the analyte, the medium in the flowpath, the strength of the electric field, and the like. Following application of the electric field between electrodes 59 and 58, which are placed in reservoirs 54 and 53 respectively, the analyte moves from intersection 51 along electrophoretic flowpath 52 towards reservoir 53 and through detection region 65.

Figure 5:
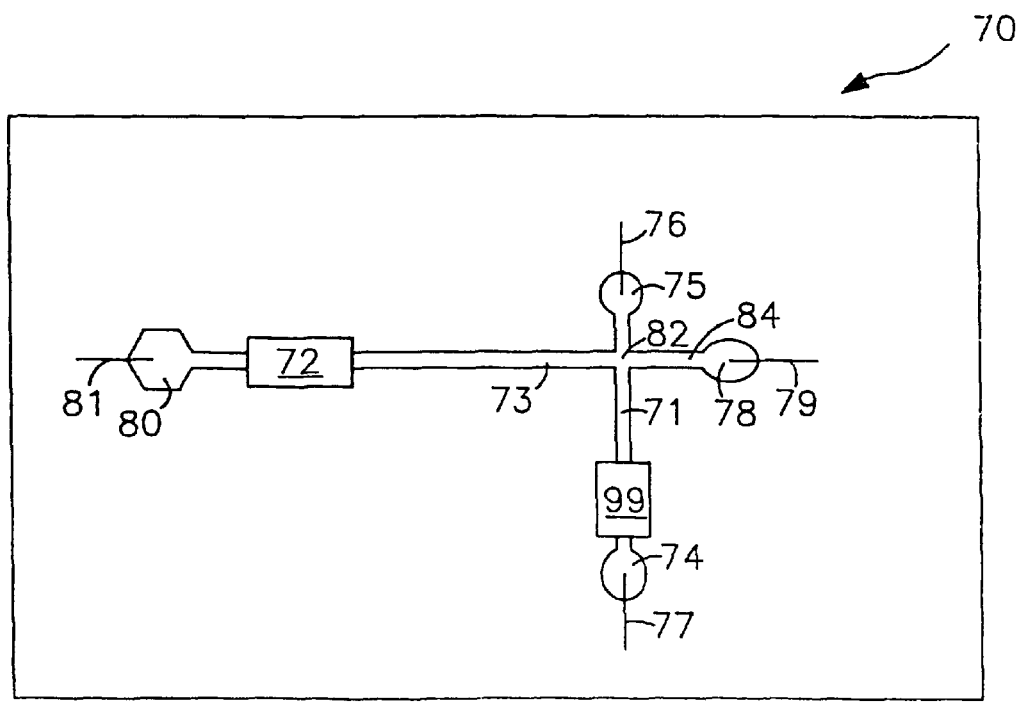
FIG. 5 provides a diagrammatic view of an embodiment of the subject invention in which the enrichment channel comprises a single fluid inlet and outlet.

FIG. 5 provides a diagrammatic top view of yet another embodiment of the subject invention in which the enrichment channel comprises a single fluid inlet and outlet. Device 70 comprises main electrophoretic flowpath 71 in intersecting relationship with secondary electrophoretic flowpath 73. Upstream from the intersection 82 along secondary electrophoretic flowpath 73 is enrichment channel 72. In using this embodiment, sample is introduced through syringe interface 80 into enrichment channel 72, whereby the analyte comprising fraction of the sample is reversibly bound to the material present in the enrichment channel. An electric field is then applied between electrodes 81 and 79 which moves the non-reversibly bound or waste fraction of the sample out of the enrichment channel 72, along secondary electrophoretic flowpath 73, past intersection 82, and out discharge outlet 84 into waste reservoir 78. An elution buffer is then introduced into enrichment channel 72 through syringe interface 80 and an electric field applied between electrodes 81 and 79, causing elution buffer to flow through enrichment channel 72 into secondary flow electrophoretic flowpath 73, carrying analyte along with it. When analyte reaches intersection 82, the electric field between electrodes 79 and 81 is replaced by an electric field between electrodes 76 and 77, which causes analyte to move along main electrophoretic flowpath 71 and towards reservoir 74 through detection region 99.

Figure 6:
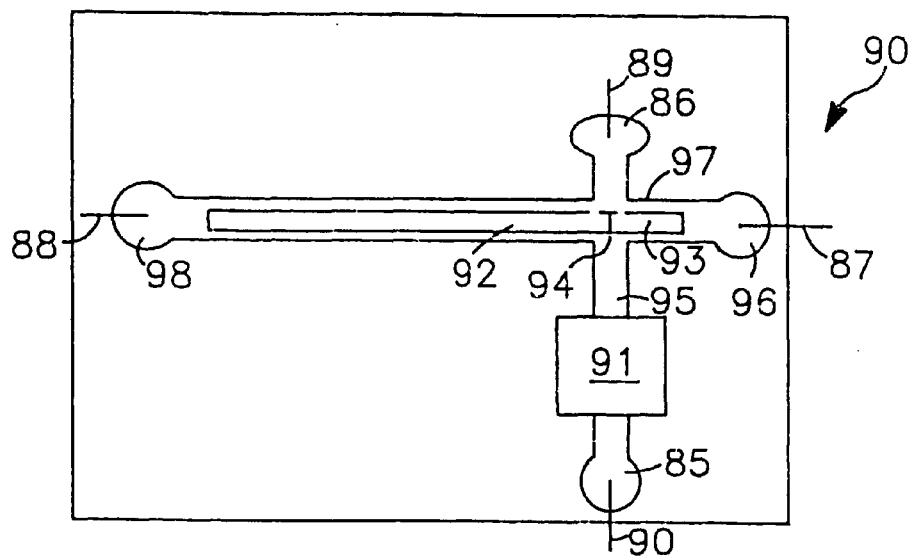
FIG. 6 provides a diagrammatic view of a device according to the subject invention in which the enrichment channel comprises an electrophoretic gel medium instead of the chromatographic material, as shown in FIGS. 1 and 2.

The device shown diagrammatically in FIG. 6 comprises an enrichment channel having an electrophoretic enrichment means, instead of the chromatographic enrichment means of the devices of FIGS. 1 to 5. In device 90, sample is introduced into reservoir 96 and an electric field is applied between electrodes 87 and 88, causing the sample to migrate towards reservoir 98. As the sample migrates towards reservoir 98 it enters stacking gel 93 having a relatively large pore size and travels towards secondary gel 92 of relatively fine pore size. At interface 94, the sample components are compressed into a narrow band. At this point, the electric field between electrodes 87 and 88 is replaced by an electric field between electrodes 89 and 90, which causes the narrow band of sample components at interface 93 to migrate into main electrophoretic flowpath 95, past detection region 91 and towards reservoir 85. In device 90, instead of the stacking gel configuration, one could provide for a molecular size membrane at the region of interface 93, which can provide for selective passage of sample components below a threshold mass and retention at the membrane surface of components in excess of the threshold mass. In yet another modification of the device shown in FIG. 6, present at the location of interface 93 could be an electrode by which an appropriate electric potential could be applied to maintain a sample component of interest in the region of 93, thereby providing for component concentration in the region of 93. For example, for an anionic analyte of interest, upon introduction of sample into reservoir 96 and application of an electric field between 93 and 87, in which 93 is the positive electrode and 87 the ground, the anionic will migrate towards and concentrate in the region of 93. After the analyte has concentrated in the region of electrode 93, an electric field can then be applied between 89 and 90 causing the anionic analyte to migrate towards reservoir 85.

Figure 7:
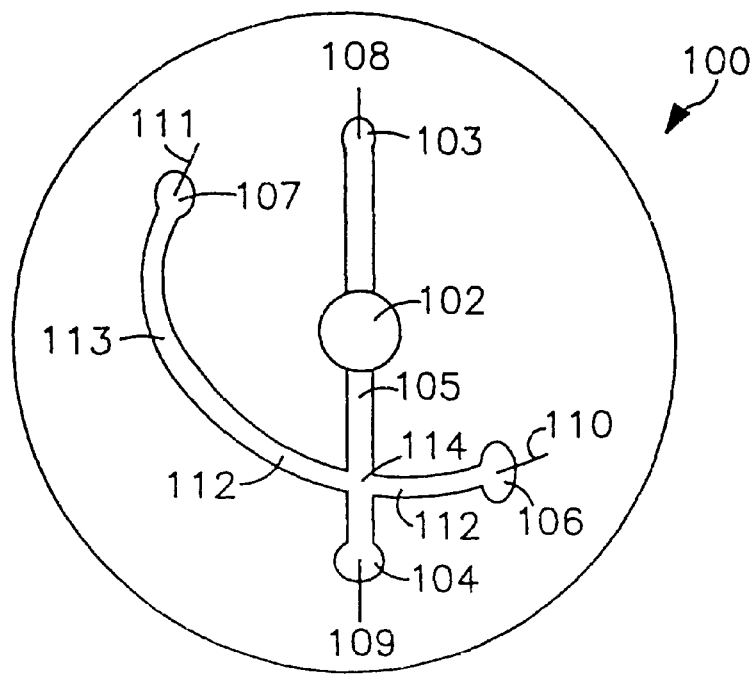
FIG. 7 provides a diagrammatic top view of disk shaped device according to the subject invention.

FIG. 7 provides a top diagrammatic view of a disk shaped embodiment of the subject device, as opposed to the credit card shaped embodiments of FIGS. 3 to 6. In device 100, sample is first introduced into enrichment channel 102. An electric field is then applied between electrodes 108 and 109, moving elution buffer 103 through enrichment channel 102, whereby analyte retained in the enrichment channel 102 is released and carried with the elution buffer to intersection 114. The electric field between 108 and 109 is then replaced with an electric field between 110 and 111, causing analyte to move from intersection 114 along main electrophoretic flowpath 112, past detection region 113 and towards reservoir 107.

Figure 8:
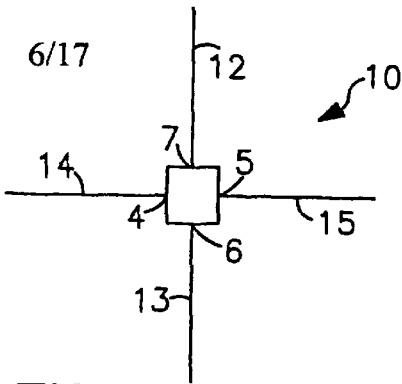
FIG. 8 is a flow diagram of a device as in FIGS. 1 or 2.

Other embodiments may be understood by reference to the flow diagrams in FIGS. 8 through 19, some of which correspond to embodiments shown in the sketches of FIGS. 1 through 7. Referring, for example, to FIG. 8, there is shown a flow diagram of an enrichment channel as shown in FIG. 1 or FIG. 2, with corresponding identification numbers. Accordingly, as described with reference to FIGS. 1 and 2, sample enters enrichment channel 10 through sample inlet 7 by way of flowpath 12. As the sample moves through enrichment channel 10 the fraction containing the fraction of interest is retained on an enrichment medium, which may be, for example, a reverse phase C18 material (as described with reference to FIG. 1) or binding pair members covalently bound to a network of glass filaments (as described with reference to FIG. 2), while the remaining waste fraction flows out through waste outlet 6 along flowpath 13. After a suitable quantity of sample has flowed through enrichment channel 10, flow through inlet 7 and outlet 6 is halted, and elution buffer enters enrichment channel 10 through inlet 4 by way of flowpath 14. Within enrichment channel 10 the retained fraction of interest is released into the elution buffer passing over the enrichment medium, and passes out through enriched fraction outlet 5 by way of flowpath 15.

Figure 9:
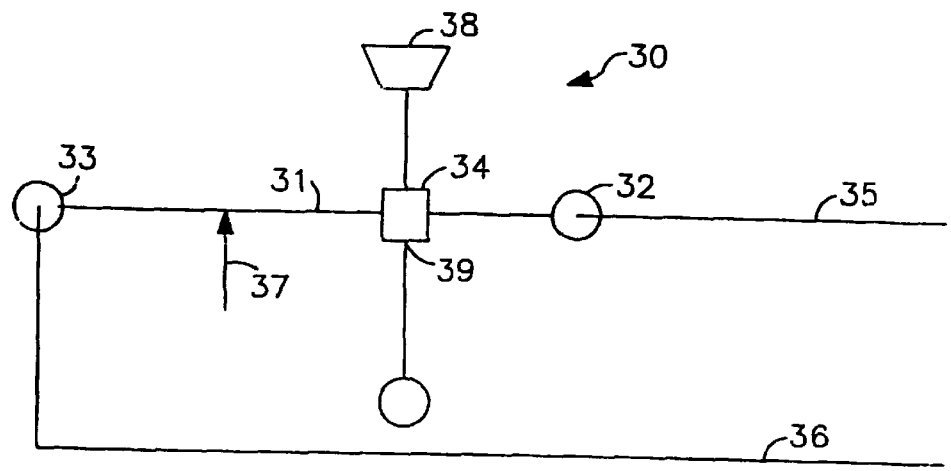
FIG. 9 is a flow diagram of a device as in FIGS. 3A, 3B.

And referring to FIG. 9, there is shown a flow diagram of the embodiment of a device 30 as sketched in two views in FIGS. 3A, 3B and described with reference thereto. In the flow diagrams, the enrichment channel (34 in FIGS. 3A, 3B, 9) is represented by a square; the various reservoirs (e.g., 32, 33 in FIGS. 3A, 3B, 9) are represented by small circles at the ends of the flowpaths (channels), which are represented by lines (e.g., main electrophoretic flowpath 31 in FIGS. 3A, 3B, 9); electrodes (35, 36 in FIGS. 3A, 3B, 9) are represented by hairlines running to the centers of the reservoir circles; an interface for syringe injection (where one may be present; e.g., 38 in FIGS. 3B, 9) is represented by a trapezoid at the end of the sample input flowpath; and the detection region (37 in FIGS. 3A, 3B, 9) is represented by a heavy arrow touching the main electrophoretic channel. Similarly, in FIG. 12, there is shown a flow diagram of the embodiment of a device 90 as sketched in FIG. 6 and described above with reference thereto. In this embodiment, the enrichment channel (120 in FIG. 12) works by electrophoretic enrichment, which results in accumulation of the fraction of interest at the point where the enrichment channel 120 is intersected by the main electrophoretic channel 95. Movement of sample material through the enrichment channel can be accomplished by application of an electrical potential difference between electrodes 87, 88; and elution of the fraction of interest from the enrichment channel through the main electrophoretic channel and to the detection region 91 can be accomplished by application of an electrical potential difference between electrodes 89, 90. As described above with reference to FIG. 6, the accumulation point can be an interface 94 between a stacking gel 93 and a secondary gel 92; and in a further modification, a suitable electrical potential can be applied at an electrode (121 in FIG. 12) at the site of the interface 93 to provide for component concentration in that region of the enrichment channel.

Figure 10:
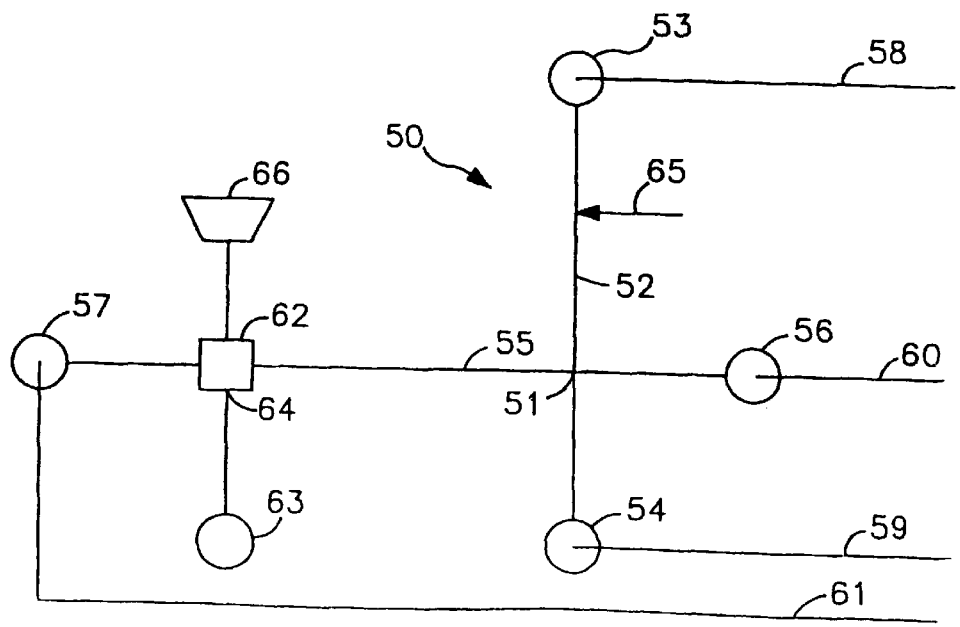
FIG. 10 is a flow diagram of a device as in FIG. 4.
Figure 13:
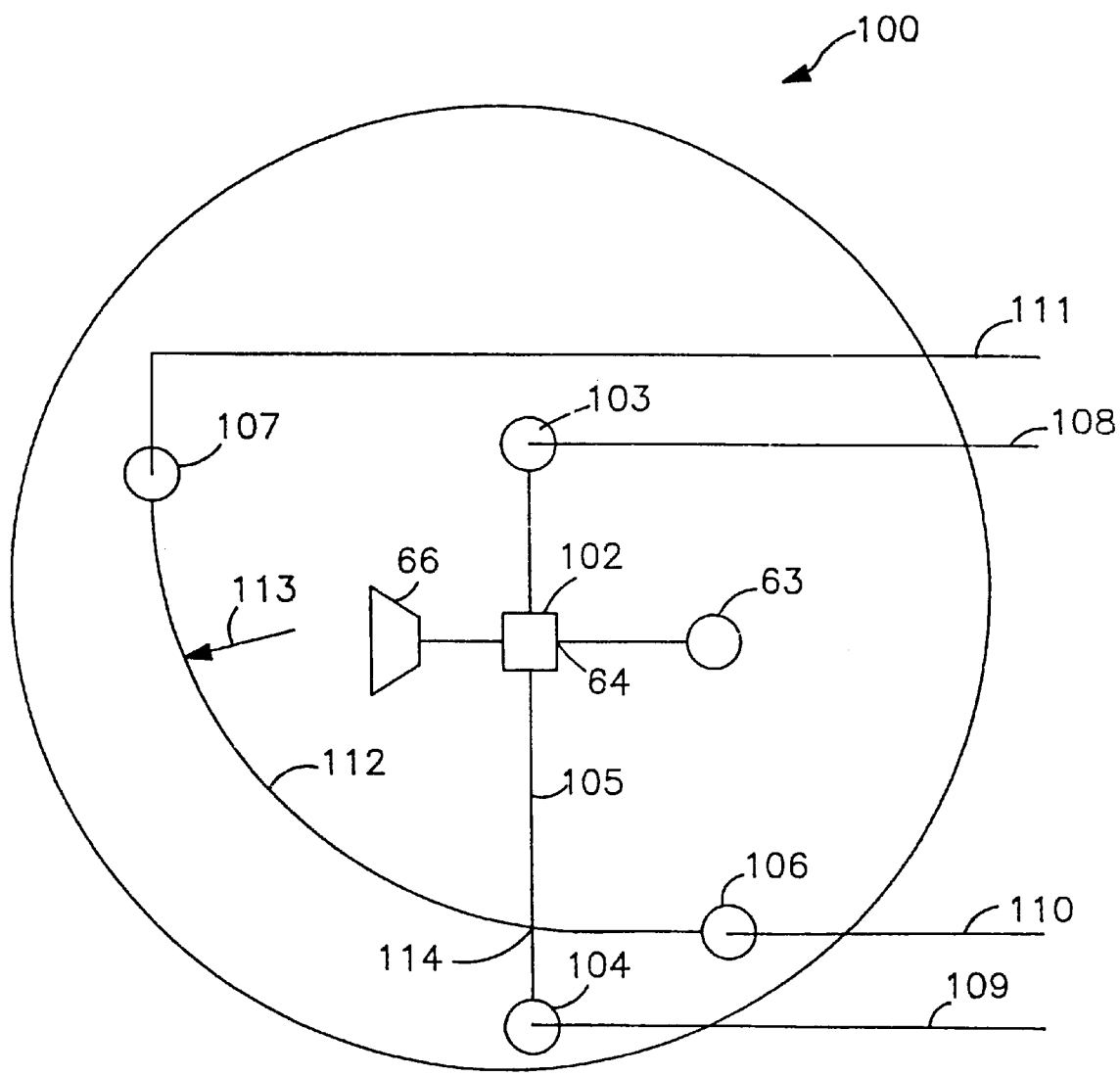
FIG. 13 is a flow diagram of a device as in FIG. 7.
Figure 14:
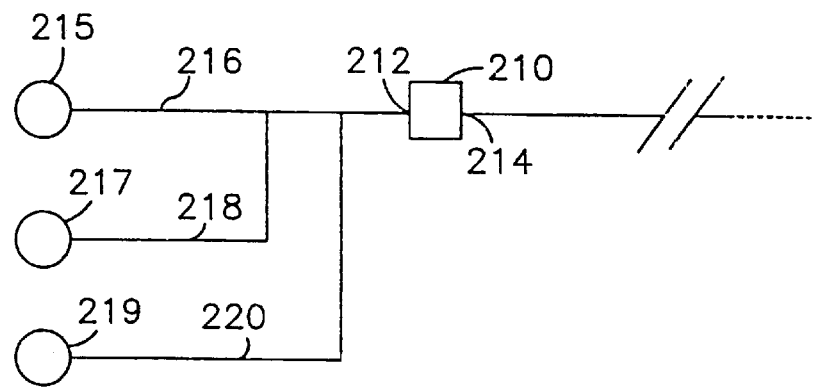
FIG. 14 is a flow diagram of part of an embodiment of a device according to the invention, showing multiple inlets to the separation channel.

FIG. 10 is a flow diagram of the embodiment of a device 50 in which the enrichment channel 62 is separated from main electrophoretic flowpath 52 by secondary electrophoretic flowpath 55, as sketched in FIG. 4 and described above with reference thereto. Similarly, FIG. 13 is a flow diagram of the disc-shaped embodiment of a device 100 as sketched in FIG. 7 and described with reference thereto. FIG. 13 shows the sample input flowpath by which the sample is introduced from the syringe interface 66 into the enrichment channel 102, and the discharge outlet 64 by which waste passes out to waste reservoir 63 while the fraction of interest is retained on the retention medium in the enrichment channel. These features are not shown in the top views of FIG. 7 or FIG. 4.

Figure 11:
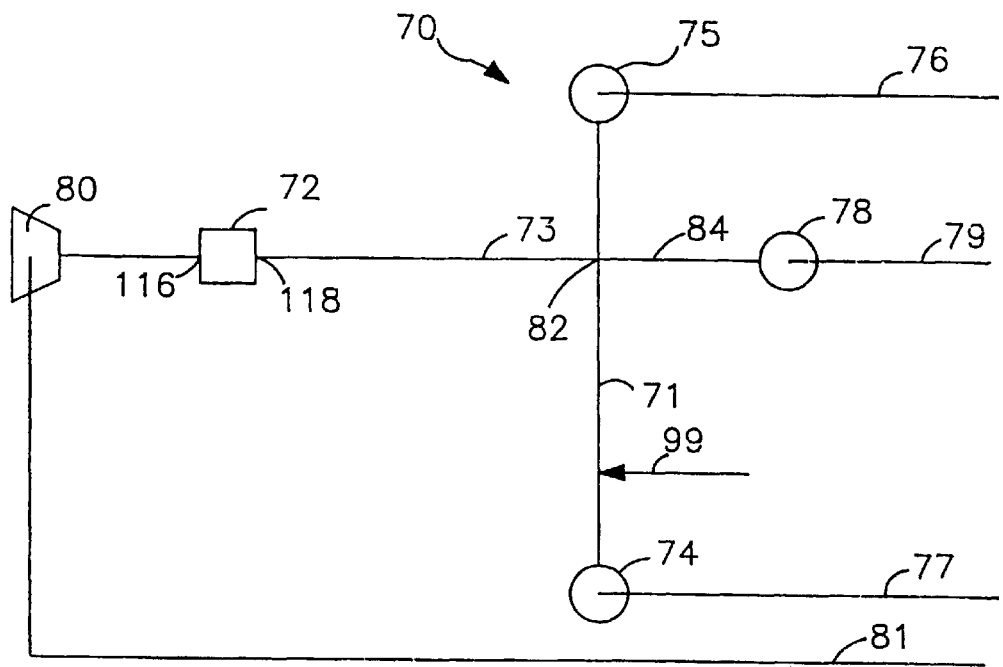
FIG. 11 is a flow diagram of a device as in FIG. 5.

In FIG. 11 there is shown a flow diagram of a device 70, in which there is only one fluid inlet into, and one fluid outlet out from, the enrichment channel 72, as sketched in FIG. 5 and described with reference thereto. During sample injection by way of the syringe interface the fluid inlet 116 serves as a sample inlet and the fluid outlet 118 serves as a waste outlet. While the fraction of interest is retained by the retention medium in the enrichment channel, the waste fraction flows downstream through the secondary electrophoretic flowpath 73, across the intersection 82 of the secondary electrophoretic flowpath with the main electrophoretic flowpath 71, and into discharge outlet 84, which directs the waste away from the mail electrophoretic flowpath 71 toward waste reservoir 78. During elution, elution buffer is injected by way of the syringe interface; fluid inlet 116 serves as an elution buffer inlet and the fluid outlet 118 serves as an enriched fraction outlet to the secondary electrophoretic channel. The fraction of interest moves into the elution buffer in which it is driven electrokinetically in an electric field produced by applying a voltage across electrodes 79, 81 to the intersection of the secondary electrophoretic channel and the main electrophoretic channel. Once the fraction of interest has reached the intersection, a voltage is applied across electrodes 76, 77 to draw the analyte or analytes in the fraction of interest into and along the main electrophoretic flowpath to the detection zone 99.

As noted with reference to FIG. 5, the waste fraction (material not bound to the enrichment medium) can be washed out of the enrichment channel and away from the main electrophoretic pathway by application of an electric field between electrodes upstream from the enrichment channel and downstream from the discharge outlet. That is, prior to introducing the elution buffer to the enrichment channel, a liquid wash medium is passed over the enrichment medium and out through the discharge outlet, carrying away waste fraction components. Any of a variety of materials can be suitable as a wash medium, so long as the wash medium does not substantially elute the fraction of interest from the enrichment medium. Moreover, the wash medium can be chosen to facilitate a selective release or removal, prior to elution, of undesired components that may be bound to or otherwise associated with the enrichment medium. For example, where the components of interest are DNA fragments, the wash medium may contain enzymes that selectively degrade proteins or polypeptides or that selectively degrade RNAs, facilitating the removal of these contaminants away from the fraction of interest prior to elution. Or, for example, where the components of interest are proteins, the wash medium may contain DNAses and RNAses.

Sequential movement of the various liquids into and through the enrichment channel can be readily controlled by providing a reservoir and a flowpath to the upstream part of the enrichment channel for each such liquid. As illustrated in the flow diagram of FIG. 14, for example, an input 212 to enrichment channel 210 is fed by a sample supply flowpath 220 running from a sample reservoir 218, by a wash medium flowpath 218 running from a wash medium reservoir 217, and by an elution medium flowpath 216 running from an elution medium reservoir 215. Movement of these materials can be selectively controlled by application of electrical potentials across electrodes (not shown the Fig.) at the respective reservoirs and at suitable points (as described herein for various configurations) downstream from enrichment channel output 214. Suitable wash media for proteins include, for example, pH-adjusted buffers and organic solvents; and washing can be effected by, for example, adjusting ionic strength or temperature of the wash medium.

Other materials may be introduced to the input flowpath as well, and, particularly, one or more reagent streams can be provided for pretreatment of the sample itself prior to moving it onto the enrichment channel. A crude sample of body fluid (blood, lymphatic fluid, amniotic fluid, cerebrospinal fluid, or urine, for example) can be pretreated by combining the sample with a reagent in the sample flowpath. For example, DNA may be released from cells in a crude sample of whole blood by admixture of a reagent containing an enzyme or a detergent.

Figure 15:
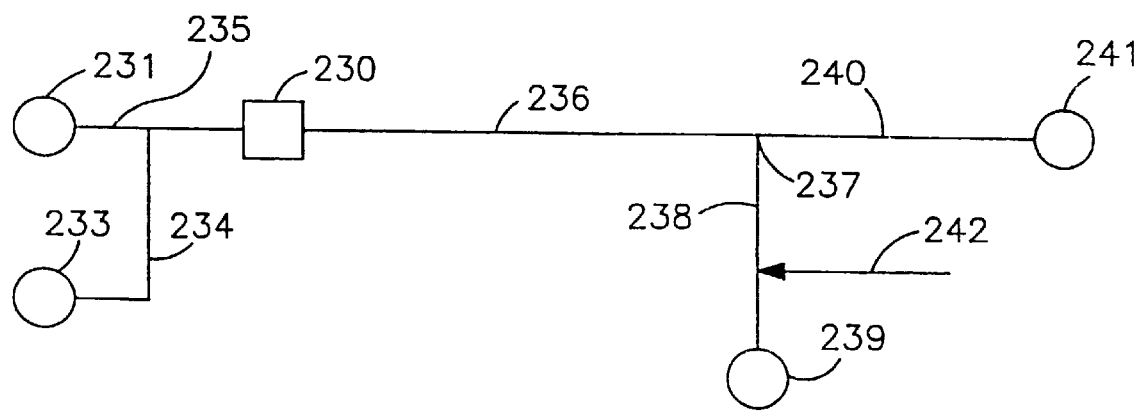
FIG. 15 is a flow diagram of an embodiment of a device according to the invention, showing an alternative configuration for the intersection between the main and secondary electrophoretic flowpaths.

Other flowpath configurations downstream from the enrichment channel can be employed, and certain of these may provide some advantages for particular kinds of downstream treatment or analysis of the components of the fraction of interest. In FIG. 15, for example, the secondary electrophoretic flowpath does not cross the main electrophoretic flowpath; rather, main electrophoretic flowpath 238 joins secondary electrophoretic flowpath 236 at a T intersection (compare, FIG. 12). In this configuration, the upstream arm of the main electrophoretic flowpath runs in the same channel as the secondary electrophoretic flowpath 236. As in other configurations, described herein, sample enters the enrichment channel 230 by way of sample flowpath 234 from sample reservoir 233; and during the enrichment stage the waste fluid passes out from enrichment channel 230 by way of secondary electrophoretic flowpath 236, then past T intersection 237 and away through discharge outlet 240 to waste reservoir 241. Once the enrichment stage is complete, a wash medium may be passed through the enrichment channel and also out through the discharge outlet. The wash medium may be introduced by way of the sample supply flowpath or, optionally, from a separate wash medium flowpath as described above with reference to FIG. 14. Movement of the sample and the wash medium can be accomplished by application of an electric field across electrodes (not shown in the Fig.) at waste reservoir 241 and, respectively, sample reservoir 233 (and, optionally, a wash reservoir). Then, an elution medium can be moved from an elution buffer reservoir 231 by way of elution buffer pathway 235 into and through enrichment channel 230, through secondary electrophoresis pathway 236. Media downstream from the eluting fraction components can be directed away from main electrophoretic flowpath 238 and out by way of waste discharge flowpath 240, until the most downstream component of interest has reached the intersection 237. Then an electrical potential can be applied at reservoir 239 to draw the components from secondary electrophoretic flowpath 236 through intersection 237 and within main electrophoretic flowpath 238 toward and through detection region 242.

Figure 12:
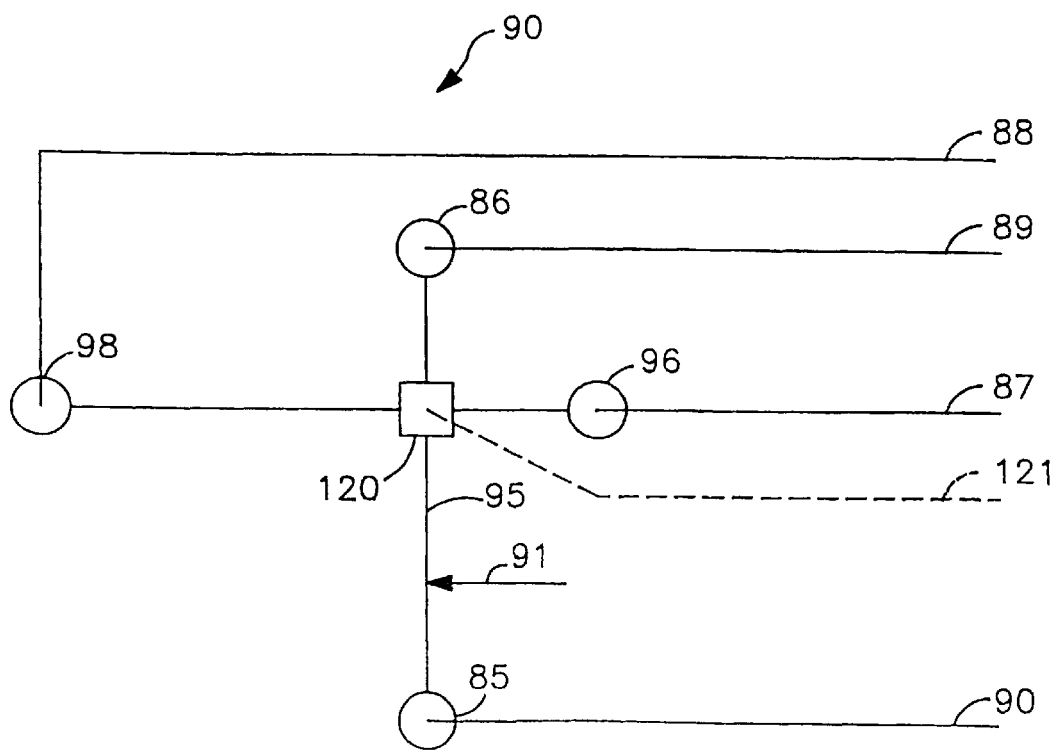
FIG. 12 is a flow diagram of a device as in FIG. 6.

An intersection of the main and secondary electrophoretic flowpaths at an "injection cross", as shown for example in FIGS. 5, 12, can be advantageous where precise metering of the sample plug is desired, as for example, where the main electrophoretic flowpath is used for electrophoretic separation. Such an injection cross can provide for injection from the intersection of a geometrically defined plug of sample components from the fraction of interest.

On the other hand, where precise control of a sample plug is not desirable, and particularly where it is desirable to move the entire eluted sample through the main electrophoretic path way, a T intersection can be preferred. Such a configuration may be advantageous where, for example, the components are analyzed by passing substantially the entire eluted fraction through an array of affinity zones downstream from the intersection.

Figure 16:
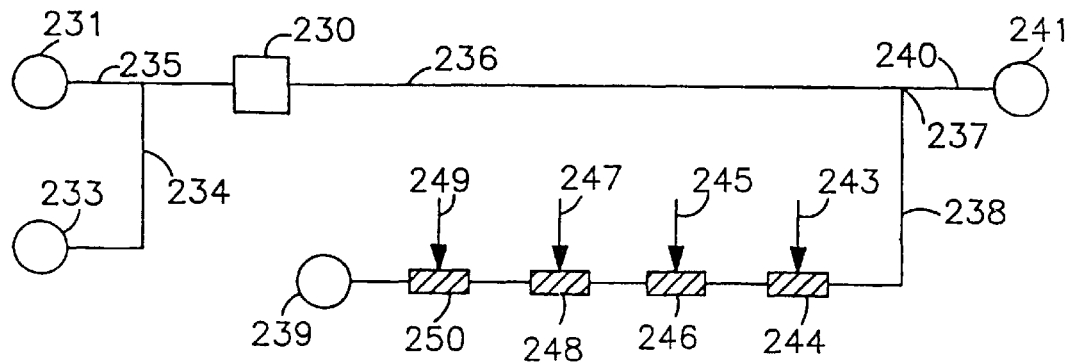
FIG. 16 is a flow diagram of an embodiment of a device according to the invention, showing a plurality of analytical zones arranged in series downstream from the enrichment channel.

By way of example, FIG. 16 is a diagram showing the flow in a configuration having a serial array of affinity zones 244, 246, 248, 250. Each affinity zone is provided with an enrichment medium that has a specific affinity for a selected component of the fraction of interest. For example, the fraction of interest may consist of DNA in a crude cell lysate, wherein the lysate may have been formed upstream from enrichment channel 230 and concentrated and/or purified in enrichment channel 230, so that the eluted fraction that passes into main electrophoretic flowpath 238 consists principally of a complex mixture of DNA fragments of different lengths and base composition. Each hybridization zone is itself an enrichment channel, in which the enrichment medium includes an immobilized oligonucleotide probe having a sequence complementary to a sequence in a target DNA. As the eluted fraction passes serially through the affinity zones 244, 246, 248, 250, any target DNA present in the fraction that is complementary to the probe in one of the affinity zones will become bound in that affinity zone. The affinity zones are provided with detectors 243, 245, 247, 249, configured to detect and, optionally, to quantify, a signal (such as fluorescence or electrochemilluminescence) from components of interest bound in the affinity zones. Any form of biomolecular recognition may be employed as a capture principle in the affinity zones, as the skilled artisan will appreciate. Useful types of affinity include antibody-antigen interactions; binding of poly-dT with adenylated RNA; oligonucleotide probes for RNA, DNA, PNA; streptavidin-biotin binding; protein-DNA interactions, such as DNA-binding protein G or protein A; and molecules having group specific affinities, such as arginine, benzamidine, heparin, and lectins. Other examples will be apparent to the skilled artisan.

Accordingly, for example, the capture principle may include receptor-ligand binding, antibody-antigen binding, etc., and thus the methods and devices according to the invention can be useful for carrying out immunoassays, receptor binding assays, and the like, as well as for nucleic acid hybridization assays.

Figure 17:
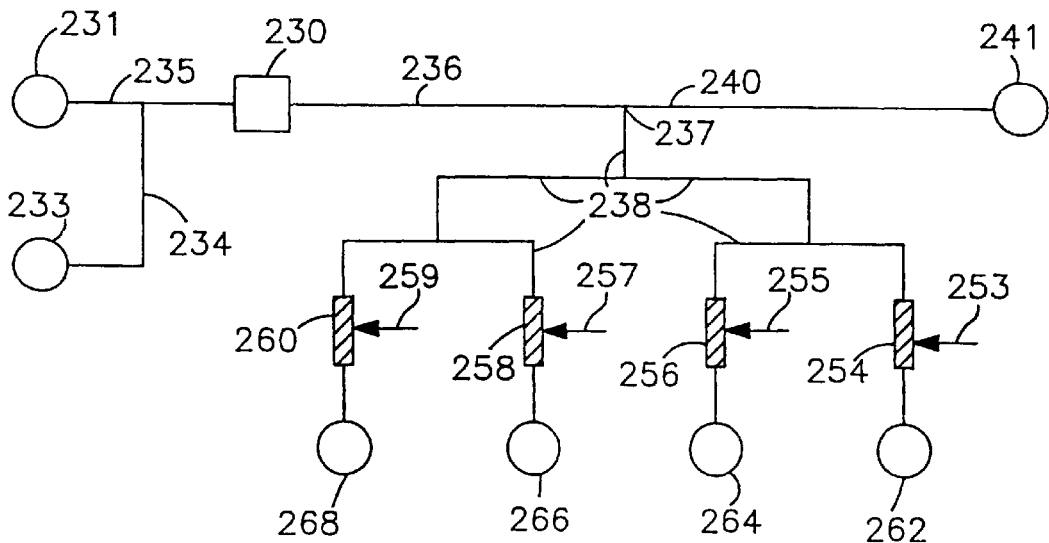
FIG. 17 is a flow diagram of an embodiment of a device according to the invention, showing a plurality of analytical zones arranged in parallel downstream from the enrichment channel.
Figure 18:
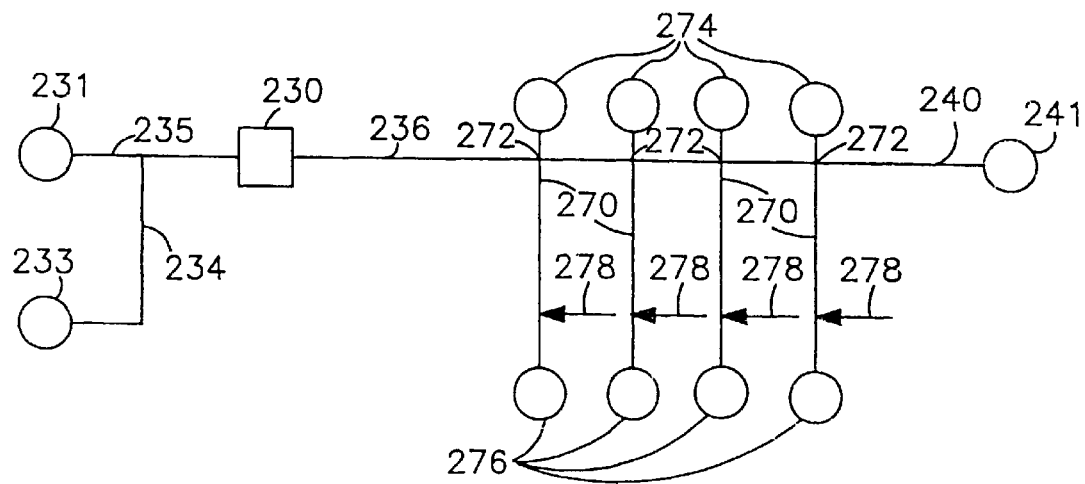
FIG. 18 is a flow diagram of an embodiment of a device according to the invention, showing a plurality of main electrophoretic flowpaths downstream from the enrichment channel.

Alternatively, as mentioned above, the main electrophoretic flowpath can be branched downstream from the intersection with the secondary electrophoretic flowpath, providing a parallel array of main electrophoretic flowpaths, as shown by way of example in FIG. 17. Electrophoretic flowpath 238 is shown as twice bifurcated, so that four main electrophoretic flowpath branches run downstream to their respective waste reservoirs 262, 264, 266, 268. The branches are provided in this example with affinity zones 254, 256, 258, 260, with detectors 253, 255, 257, 259. Pertinent properties of the milieu (such as, e.g., temperature, pH, buffer conditions, and the like) can advantageously be controlled in each flowpath branch independently of the others, as is shown in more detail with reference to FIG. 22, below.

Where the affinity zones are arranged in parallel, as for example in FIG. 17, each affinity zone receives an aliquot of the entire sample that is delivered to the main electrophoresis channel. In this embodiment, sample components that can be captured by two or more of the affinity media will appear in the respective two or more affinity zones. For example, a nucleic acid fragment that contains either one or both of two sequences complementary to two of the probe sequences will, in the parallel arrangement, be captured in the two affinity zones containing those two probes. On the other hand, where the affinity zones are serially arrayed, as for example in FIG. 16, each downstream affinity zone is reached only by sample components not captured by an affinity zone upstream from it. Here, for example, a nucleic acid fragment that contains both of two sequences complementary to probe sequences in two of the affinity zones will be captured only in the more upstream of the two affinity zones. This arrangement may be advantageous where it is desirable to identify sample components that contain one but not another moiety or sequence.

And alternatively, as noted above, a plurality of main electrophoretic flowpaths may be provided for treatment of the enriched eluted sample. As shown by way of example in FIG. 18, the main electrophoretic flowpaths 270 may carry eluted sample fraction from the secondary electrophoretic flowpath 236 through a series of intersections 272. Each main electrophoretic flowpath 270 is provided with reservoirs upstream (274) and downstream (276) and each is provided with a detector 278. This configuration may be employed to run a set of tests or assays or measurements on aliquots of a single enriched sample fraction, and will be particularly useful where, as noted above, precise metering of the quantity of analyte is desirable. As will be appreciated, each of the main electrophoretic flowpaths 270 can be provided with an affinity zone or with an array of affinity zones (not shown in FIG. 18) as described above with reference to FIGS. 16, 17.

Figure 19:
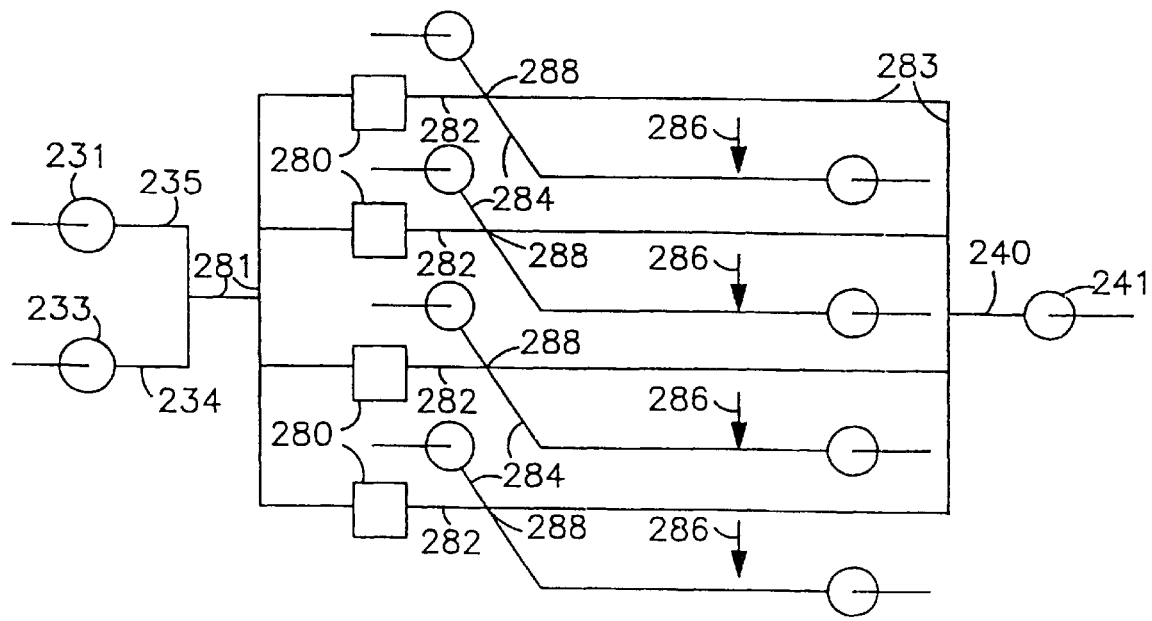
FIG. 19 is a flow diagram of an embodiment of a device according to the invention, showing a plurality of enrichment channels arranged in parallel.

Or, as shown by way of example in FIG. 19, a plurality of enrichment channels 280 can receive sample from a branched sample supply manifold 281. Each enrichment channel 280 can during the elution stage deliver an enriched fraction to an intersection 288 with a main electrophoretic flowpath 284. During the enrichment stage (and optionally during a wash stage) waste fraction is carried away from the intersections 288 by way of a branched discharge manifold 283 and out through discharge outlet 240 to waste 241. Such an arrangement can be used to particular advantage, for example, where the fraction of interest is a mixture of DNAs, and where it is desirable to obtain both sequence information and size information for the DNAs. The configuration of FIG. 19 can be used, for example, for a flow-through analysis analogous to a Southern blot analysis. In the conventional Southern blot analysis, DNA fragments are first separated on a gel, and then transferred to a membrane on which probes are allowed to bind complementary fragments. The Southern blot analysis is practiced mainly as a manual bench-top procedure, and is highly labor-intensive, taking several days to complete. The flow-through analysis, according to the invention, can be substantially automated, and the analysis can be completed much more rapidly.

In the flow-through analysis, each but one of the enrichment channels is provided with a sequence-specific capture medium, such as a sequence-specific immobilized oligonucleotide probe, and the last one of the enrichment channels is provided with a generic capture medium which binds all DNA fragments in the sample. These different enriched fractions are delivered to the intersections 288 during the elution stage, and then they are moved electrophoretically in the respective main electrophoretic flowpaths 284, each provided with a detector 286. The enriched fraction from the enrichment channel containing a generic capture medium contains a mixture of all sizes of DNAs from the sample, having a range of electrophoretic mobilities, passing the detector sequentially, and resulting in a series of signal peaks. The enriched fraction from each of the other enrichment channels contains only DNAs complementary to the specific capture medium in its respective enrichment channel.

The use of affinity binding agents on particulate supports can, in certain configurations of flowpaths, provide for highly efficient separation of a selected subset of biological entities from among two or more subsets in a mixed population of biological entities, where each subset has a characteristic determinant. For example, several enrichment channels, or affinity zones, in each of which is held a capture agent capable of selectively binding a determinant on a subset of biological entities, can be arranged in parallel. The capture agents include a first capture agent comprising a receptor which specifically binds, either directly or indirectly, to the characteristic determinant of the first subset, and at least a second capture agent comprising a receptor which specifically binds, either directly or indirectly, to the characteristic determinant of at least one other subset. The subset to which each capture agent binds is the target subset of each capture agent. A sample of the mixed population of biological entities is contacted with the plurality of capture agents, under conditions favoring specific binding of the receptor of the first capture agent to the first subset, and of the receptor of the second capture agent to at least one other subset, where at least one of the capture agents is dissociably bound to its respective subset.

The bound subsets are next separated from the sample and from any subset of the population of biological entities that is not bound to a capture agent. One of the dissociably bound subsets is thereafter dissociated from the capture agent to which it is bound, and is thereafter isolated. The isolated, selected subset is normally recovered for further processing, which may include analysis and/or propagation.

These dissociation and isolation steps as described above may be repeated to yield a second or third selected subset, and so on, if desired, provided that dissociation of the one capture agent from its target subset does not result in dissociation of another capture agent from its selected target subset.

According to the device and method of this embodiment of the invention, operating parameters and device configuration enable successful performance of biological and other separations not heretofore attainable. In conventional affinity separations, wherein a ligand is attached directly to a stationary solid support, such as in affinity chromatography, capture and separation of the target substance are simultaneous events. For separations using a particulate magnetic capture agent, as in an embodiment of the present invention, these two events are separate. The bifurcation of these two events according to a preferred embodiment of this invention affords significant advantages.

In the method of the invention, affinity-binding reactions are coupled with respective specific cleavage reaction. Thus, by creating affinity-binding/cleavage pairs, two distinct specificities for each separation procedure result. When it is desired to separate one or more selected subset of biological entities from a mixed population of such entities on a collection surface, this additional parameter allows permutations of events, such that separations which were either difficult or impossible can be carried out according to the invention with relative ease.

Prior to the invention, a notable obstacle to the use of particles for the separation and subsequent release of distinct, selected subsets from a mixed population of biological entities has been that the biological entities must be collected in such a manner as to allow the selected subset to be removed from the mixed population without appreciable contamination from non-selected substances. In the practice of the present invention, this difficulty is overcome in two ways. One is in the design of the integrated microfluidic device configuration. By the use of apparatus and methods described in the above-referenced U.S. Ser. Nos. 08/690,307 and 08/902,855, which are commonly owned with the present application, and which are incorporated by reference in the present application as if set forth herein in full, it is possible to circumvent the contamination problem. For example, a multiple parallel microchannel configuration provides for highly efficient separations. The second way involves the high degree of control that is afforded over the collection of the biological entities, such that after an individual affinity bond between the biological entity and the solid support is cleaved, which may be either before or after resuspension of the collected biological entities, a second collection of the particles results in segregation of the original mixed population with the exception of the subset of biological entities that was bound by the specific receptor which was selectively released from its target subset via bond cleavage.

Unlike the methods described for example in U.S. Pat. No. 5,646,001, which is incorporated by reference in the present application as if set forth herein in fill, the present invention is not limited to the selected control and manipulation of the physiochemical environment associated with bond breaking and deposition of the captured biological substances. Instead, a multiplexed microfluidic configuration provides enormous flexibility in the design of integrated devices for the separation of mixtures of biological components. Thus, a combination of both approaches may be utilized in cases when multiple subsets of biological entities are to be isolated from a mixed cell population which vary greatly in frequencies.

Figure 27:
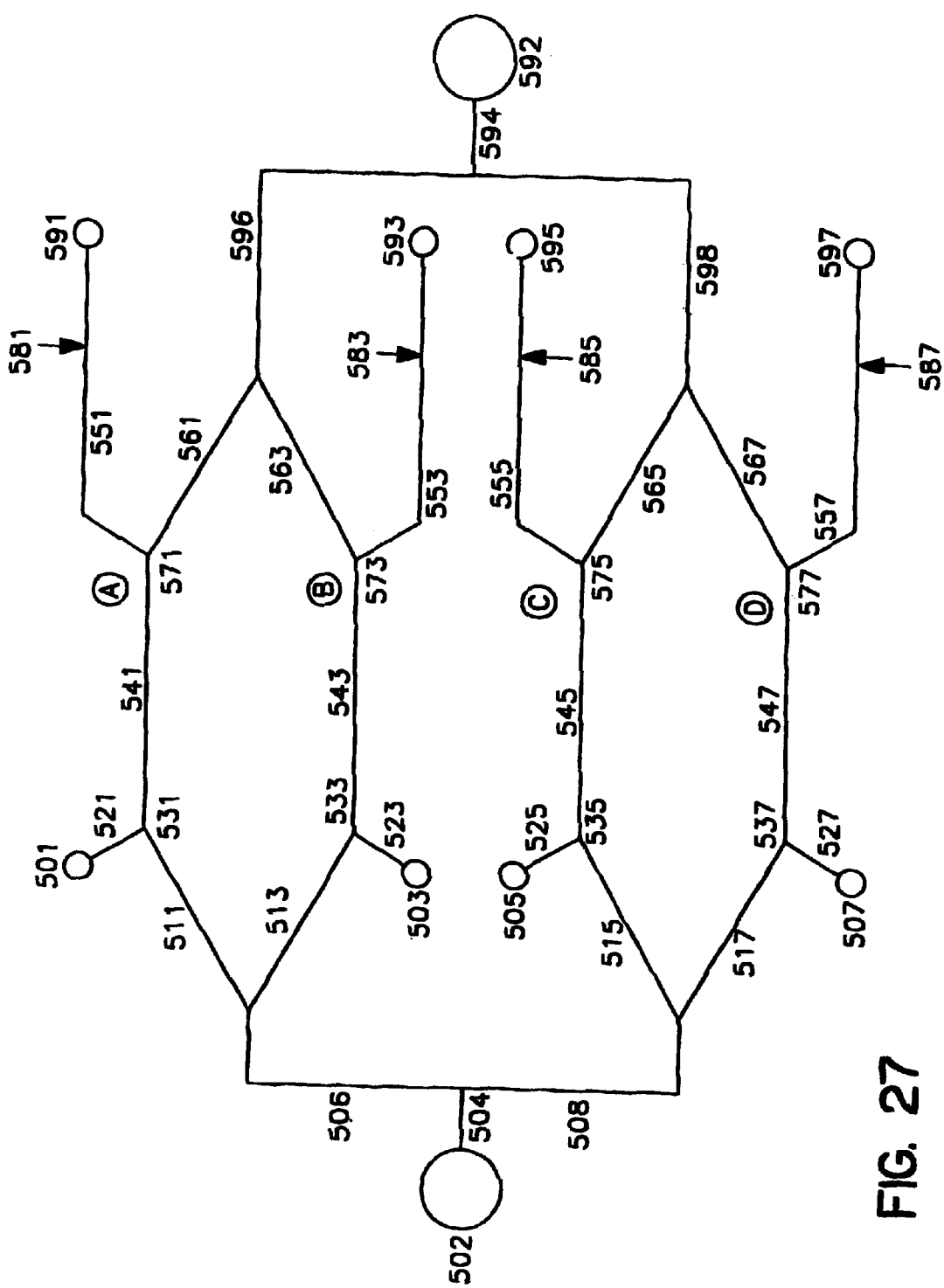
FIG. 27 is a flow diagram of an embodiment of a device according to the invention, as may be used to separate a mixture of biological entities into four different subsets, by way of affinity-binding capture and release in affinity zones arranged in parallel.

Reference is now made to FIG. 27, showing a configuration of flow paths in a microfluidic device according to the invention that can be used for separation of a mixture of five different biological entities (here, different cell types presenting as determinants different cell surface receptors) into four separate subsets.

The separation device and method provide for efficient isolation of any of a broad range of biological entities, which may be a components of a test sample or specimen capable of selective interaction with a receptor or other specific binding substance. The term "biological entity" as used herein refers to a wide variety of substance of biological origin including cells, and cell components such as membranes, organelles, etc., microbes, viruses, as well as molecules (e.g., proteins) and macromolecules (e.g., nucleic acids, including RNAs, DNAs and PNAs).

The biological entities of interest may be present in test samples or specimens of a wide range of origins, including for example biological fluids or extracts, food samples, environmental samples, etc.

The term "determinant" is used here in a broad sense to denote any characteristic that identifies or determines the nature of of an entity. When used in reference to any of the above-described biological entities, determinant means that portion of the biological entity involved in and responsible for selective binding to a specific binding substance, the presence of which is required for selective binding to occur.

The expression "specific binding substance" as used herein refers to any substance that selectively recognizes and interacts with the characteristic determinant on a biological entity of interest, to the substantial exclusion of determinants present on biological entities that are not of interest.

The capture agents used in the affinity binding separations-include a specific binding agent, or receptor, attached to a solid support. The solid support may be either stationary or mobile. Useful mobile solid phases include, for example, beads and particles. Particulate solid supports are preferably made from magnetic material to facilitate capture of the target subsets by application of a magnetic field.

In a microfluidic device configured generally as illustrated in FIG. 27, and described with reference thereto, a heterogeneous mixture of biological entities is separated into sub-populations as characterized by the determinants of the constituents of the sample.

As employed for isolation and purification of a subsets of a two or more subpopulations of cells in a mixed populaiton in a sample, the method is simple, rapid and reliable. Antibodies specific to corresponding cell surface antigens serve as capture reagents for isolating the specific targets from complex mixtures. The mixed population of biological entities may also include, but is not limited to, whole cells presenting cell surface receptors, cell membranes bearing cell surface receptors, soluble receptors, enzymes, antibodies, and specific nucleic acid sequences. Thus, a wide variety of applications involving cell biology, molecular biology, tissue typing, and microbiology are therefore possible.

The integrated device as shown in FIG. 27 includes duplicate flow patterns configured in four parallel networks of microchannels (denoted A, B, C, and D) for illustration purposes. A highly multiplexed configuration comprising of many parallel networks (more than four) is, as will be appreciated, contemplated within the invention. Similar in design to the flow configuration of FIG. 15, each microfluidic network includes a capture channel (or "enrichment zone"), having specific capture reagents (in this case, immobilized antibodies), in fluid communication with two inlet and two outlet flowpaths. With reference now to network, a the inlet and outlet flow paths join the capture channel 541 at intersections 531 and 571, respectively. One inlet flowpath is supplied by sample inlet reservoir 502, which serves as the common inlet for the entire device, and microchannels 504, 506, and 511. The other inlet flowpath, specific to network A, comprises elution buffer reservoir 501 and microchannel 521. One outlet flowpath comprises the common outlet reservoir 592 and microchannels 561, 594 and 596. The other outlet flowpath comprises of the analysis channel 551, outlet reservoir 591 and the detection zone 581.

The three stage cell isolation process, including affinity capture, release and detection, is initiated by injecting a complex mixture of biological cells into the multiplexed flow pattern as schematically illustrated in FIG. 27. Sample handling on the microfluidic device is achieved electrokinetically by controlling the electric potential across the appropriate electrodes (not shown in FIG. 27) placed within the inlet and outlet reservoirs. Within the enrichment zones, cells are captured by means of antibodies immobilized to the surface of the channels that recognize specific cell surface antigens. Alternatively, immunomagnetic beads may be employed for cell capture. In this case, the heterogeneous suspension of cells bind the target (e.g., antibodies to cell surface antigens) by specific absorption to the particular capture moieties on the surface of the beads. Immobilization of the target-bead complex to the side of enrichment chambers can then be achieved magnetically.

Using the device as illustrated in FIG. 27, a mixture of, e.g., six different cell types can be separated into four distinct subsets when bound to capture agents including four antibodies having different binding specificities. In this example, antibodies to cell surface antigens denoted by A, B, C, and D are immobilized in channels 541, 543, 545, and 547, respectively. As will be appreciated, each of the enrichment channels 541, 543, 545, and 547 has associated with it a corresponding set of intersecting inlet and outlet flowpaths and reservoirs, analysis channels and detection zones. Thus, cells denoted A, B, C, and D arising from their respective surface antigens are captured in the above-referenced channels within the microfluidic networks A, B, C and D. The remaining cells are passed through the device and collected in the common outlet reservoir 592. The remaining cells may then be used in various applications as described further below.

Upon completion of the capture step, a wash medium contained within wash buffer reservoirs (not shown in the FIG. 27) may be used to rinse the immobilized cells. The isolated cells captured in their respective enrichment zones can next be released and then analyzed within the detection zones 581, 583, 585, and 587 by electrokinetically pumping elution buffer from reservoirs 501, 503, 505, and 507 to the outlet reservoirs 591, 593, 595, and 597, respectively. Depending on the demands of the analyses and the particular application, the detection zones may simply be an optical detector, e.g., fluorescence detector or the like, or it may represent a further flow configuration. Finally, this embodiment of the invention affords an advantageous means for isolating and enriching the target biomolecules from a sample mixture.

Although the affinity-capture microchannels shown in FIG. 27 are in a parallel configuration, a single heterogeneous enrichment zone may alternatively be employed with a plurality of receptors (e.g., in this case, antibodies specific to the cell surface antigens) immobilized to the affinity channel. Heterogeneous capture and release methods are described in, e.g., U.S. Pat. No. 5,646,001 to Terstappen et al., which is incorporated herein by reference in its entirety. However, an advantage of the parallel approach is that separate homogeneous capture zones minimize the physical impact on the biological entities. This is especially important when working with whole cells, which can be very sensitive to the various elution buffers and/or thermal cycling that may be required to cleave and/or dissociate the selected subset of a mixed population of biological entities. In addition, an affinity-capture method utilizing a single enrichment column with a plurality of receptors is possible only provided that the bond linking one capture agent to a selected target subset is differentially dissociable from the bond linking the other capture agents to their respective, selected target subsets, such that dissociation of the one capture agent from its target subset will not result in dissociation of another capture agent from its selected target subset. Thus, precise manipulation of the physiochemical conditions (e.g., ionic strength, pH and concentration of a particular cleaving reagent) is easier to achieve in individual microchannels of the parallel format. As a further advantage of the device and method of the invention for separating viable cells, is that in the microfluidic platform large air bubbles—detrimental to recovery of viable cells—do not form in the fluid pathway in which the cells are manipulated.

A further significant advantage of the microfluidic devices and methods of the present invention includes the integrated systems capabilities which enable multiplexed cellular analyses to be performed on-line with the cell purification process. For example, a portable self-contained microfluidics cartridge similar to that illustrated schematically in FIG. 27 may be employed in parallel with a conventional high gradient magnetic separation (HGMS) device, as discussed below, for the rapid, quantitative and simultaneous measurement of a panel of tests to aid in the diagnosis and treatment of human disease. As an alternative to the HGMS approach, a microfluidics based method and apparatus comprising a massively parallel channel configuration provides for economical, high throughput cell purification combined with integrated cellular diagnostics. In addition, this automated process is not laborious and time consuming as are conventional cell isolation methods.

The present invention also broadly encompasses methods of using integrated microfluidic devices to deplete selected cells from a sample. High gradient magnetic separation (HGMS) has been used for the removal of magnetically labeled cells from suspensions of bone marrow, peripheral and/or cord blood cells. See, U.S. Pat. Nos. 5,514,340 and 5,691,208, which are incorporated herein by reference in their entireties. HGMS methods typically involve placing a filter of fine magnetizable wires in a strong magnetic field. High gradient magnetic fields are produced around the wires, allowing the capture of even very weakly magnetic particles upon the magnetizable wires.

Unlike the HGMS device described in U.S. Pat. No. 5,514,340, the present invention contemplates a microfluidic-based cell purification or cell purging apparatus and method for recovering hematopoietic stem/progenitor cells from bone marrow, peripheral and cord blood and/or hematopoietic tissue for transplantation. Existing HGMS methods commonly employ a three stage process to achieve cell selection. Magnetically conjugated antibodies are used to specifically target the desired cells in a mixed population of cells. The noncaptured cells that have been treated in the purification process can then be used for numerous purposes, including, e.g., bone marrow/stem cell transplantation. The integrated chip-based cell-sorting device and method includes: 1) the flow-through incubation of selected cells and antibodies specific to cell surface antigens; 2) the addition of surface-activated magnetic beads which bind with the antibodies followed by another flow-through incubation step; 3) application of a magnetic field for the affinity capture of the bead-antibody-cell complex; and 4) the magnetic release of the complex or the chemical elution/thermal dissociation of the antibody-cell surface antigen bond. The device may be employed not only to deplete but also to further analyze the unwanted "selected" cells (e.g., T cells, tumor cells or oncotopes) from a mixed population. Analyses may include, but are not limited to, cell counting, cell staining, cell sorting, cell lysis, genetic testing, competitive binding and/or "sandwich" assays employing fluorescent or other like means for detection. These assays have applications in immunodiagnostics, characterizing receptor-ligand affinity interactions and DNA hybridization reactions.

The release of cells from affinity matrices as described in U.S. Pat. No. 5,081,030, and multi-parameter cell separation using releasable colloidal magnetic particles as described in, e.g., WO 96/31776 are incorporated herein by reference in their entireties.

The invention provides means for the automated electroactive control of the fluid circuitry without requiring the use of mechanical valves, as described in U.S. Pat. No. 5,691,208. Electrokinetic pumping methods and devices are described in, e.g., U.S. Ser. No. 08/615,642, filed Mar. 13, 1996 (Attorney Docket No. A-63053-4) the disclosure of which is hereby incorporated herein by reference in its entirety.

Monoclonal antibodies that recognize a stage-specific antigen or immature human marrow cells and/or pluripotent lymphohematopoietic stem cells may be employed as described in, e.g., U.S. Pat. No. 4,714,680, which is incorporated herein by reference in its entirety.

Figure 20:
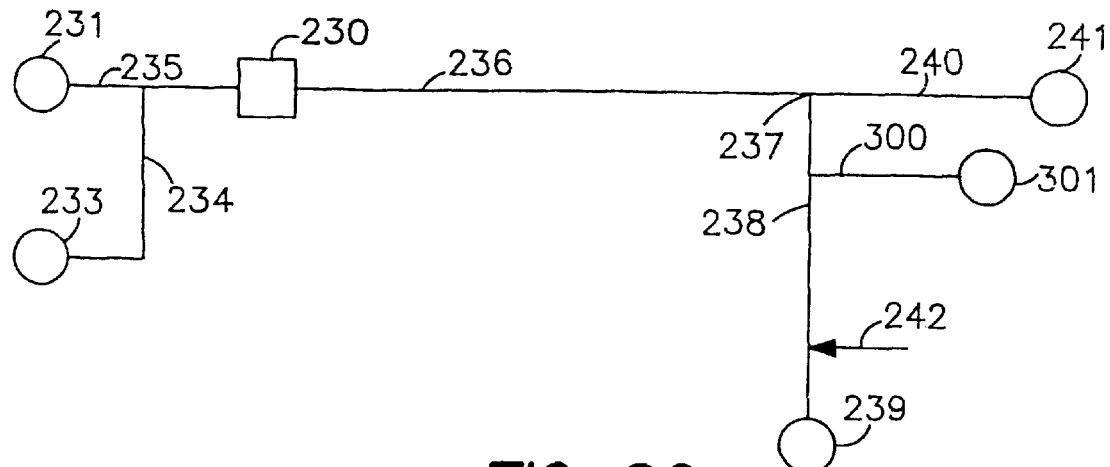
FIGS. 20 and 21 are flow diagrams of embodiments of a device according to the invention, similar to those shown in FIGS. 15 and 16, respectively, and additionally having a reagent flowpath for carrying a reagent from a reservoir directly to the main electrophoretic flowpath.

As will be appreciated, where three or more outlet reservoirs are provided, as for example is shown in FIG. 20, above, affinity capture and release can be effected, where one of the downstream reservoirs collects the purified or processed sample mixture. To provide the introduction of the selected second or competing binding pair member to release the bound entities of interest, additional input reservoirs upstream from the enrichment channel or affinity zone can be provided, as shown for example in FIG. 14.

The device of the invention may be used to deplete selected cells from a sample, such as cells which express cell surface antigens recognized by antibodies, preferably monoclonal antibodies. In one embodiment of the invention the method is used to deplete selected cells from cell suspensions obtained from blood and bone marrow. In particular, the method may be used to deplete tumor cells from bone marrow or blood samples harvested for autologous transplantation, or deplete T lymphocytes from bone marrow or blood samples harvested for allogeneic transplantation. The device of the invention may also be used to remove virus particles from a sample.

The device and methods of the invention may be used in the processing of biological samples including bone marrow, cord blood and whole blood.

The device and methods of the invention are preferably used to deplete or purge tumor cells or T lymphocytes from samples to prepare hematopoietic cell preparations for use in transplantation as well as other therapeutic methods that are readily apparent to those of skill in the art. For example, in the case of an autologous transplant, bone marrow can be harvested from a patient suffering from lymphoma or other malignancies, the sample may be substantially depleted of any tumor cells using the device and methods described herein, and the resulting hematopoietic cell preparation may be used in therapeutic methods. Bone marrow or blood can also be harvested from a donor in the case of an allogenic transplant and depleted of T lymphocytes by the methods described herein.

Using the method of the invention it is possible to recover a highly purified preparation of hematopoietic cells. In particular, a hematopoietic cell population containing greater than 50% of the hematopoietic cells present in the original sample, and which is depleted of T lymphocytes or tumor cells in the original sample by greater than 2 logarithms may be obtained. The hematopoietic cells in the preparation are not coated with antibodies or modified making them highly suitable for transplantation and other therapeutic uses that are readily apparent to those of skill in the art.

The method and device of the invention may also be used to remove red blood cells from samples such as blood and bone marrow. Half of the volume of normal blood consists of mature red blood cells. Typically these cells exceed nucleated cells by >100 fold. For many clinical and research applications, removal of red blood cells with higher recovery of cells than conventional methods such as Ficoll-Hypaque density centrifugation.

In a particular application of the invention, samples may be processed using the methods and device described herein for diagnostic flow cytometry of leukocyte subpopulations. For example, the methods may be used to prepare blood samples of patients infected with the Human Immuno Deficiency (HIV) virus for monitoring lymphocyte populations in such patients. Enumeration of the absolute numbers of leukocyte subpopulation by conventional immunofluorescence measurements and flow cytometry has been complicated by the abundant presence of red blood cells in peripheral blood and consequently, such enumeration is most often derived from separate measurements of nucleated cells numbers and immunophenotype. A variety of procedures have been proposed and are used to remove red blood cells from blood for immunophenotypic measurements but these procedures are labor intensive and difficult to automate and in some cases the procedure itself may interfere with immunofluorescence measurements. In contrast, the present invention provides an efficient and direct method for removing red blood cells from blood samples that can readily be automated as no centrifugation or wash steps are involved.

Specific Examples of uses to which the invention may be put include: Depletion of CD3+T cells from allogeneic bone marrow using the device of the invention for the prevention of graft versus host disease (GVHD); Isolation of hematopoietic progenitor cells and depletion of malignant cells in patients with B-lymphoid malignancies; Removal of CD45RA+lymphoma cells from bone marrow; Purging of breast cancer cells from peripheral blood and bone marrow; Purification of CD34+cells by immunomagnetic removal of CD34–cells; Depletion of murine cells that express lineage markers; Immunomagnetic removal of red blood cells; Cellular diagnostics—employing a microfluidic-based panel of tests; Isolation of fetal nucleated erythrocytes from maternal blood; Isolation of genetically modified hematopoietic stem cells and depletion of malignant cells of non-hematopoietic origin—as for gene therapy, for instance; Isolation and enumeration of selected cell populations of the hematopoietic cell lineages; Graft engineering for transplant; Capture of DNA and subsequent selective release of DNA recognized by probes with specific sequences; AFLP analysis; Solid-phase sample clean-up of DNA sequencing products employing immune release (desbiotin fluorophore); and others.

In some embodiments it may be desirable to combine one or more reagents with the enriched fraction downstream from the intersection of the secondary flowpath and the main electrophoretic flowpath. FIG. 20 is a flow diagram similar to one shown in FIG. 15. In FIG. 20 a reagent flowpath 300 carries a reagent (or reagents) ftom a reservoir 301 to the main electrophoretic flowpath 238, where the reagent can combine with and react with one or more analytes in the enriched fraction. And, as will be appreciated, where the main electrophoretic flowpath is branched downstream from the intersection with the secondary electrophoretic flowpath, producing subfractions in the branches, each such downstream branch can be provided with a reagent flowpath carrying reagent from a reservoir. Such a configuration can provide either for replicate treatment of the subfractions with a single reagent, or for treatment of each subfraction with a different reagent, or for simultaneous treatment of subfractions with two or more reagents, each producing a particular desired result upon interaction with the analyte(s) in the enriched subfraction.

Figure 21:
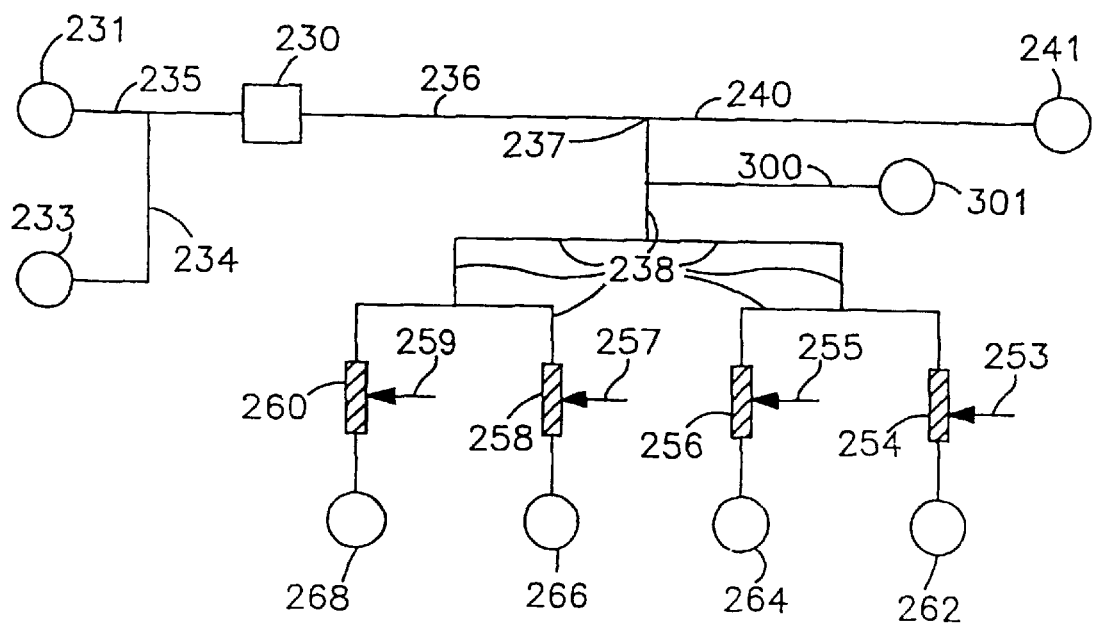
Figure 22:
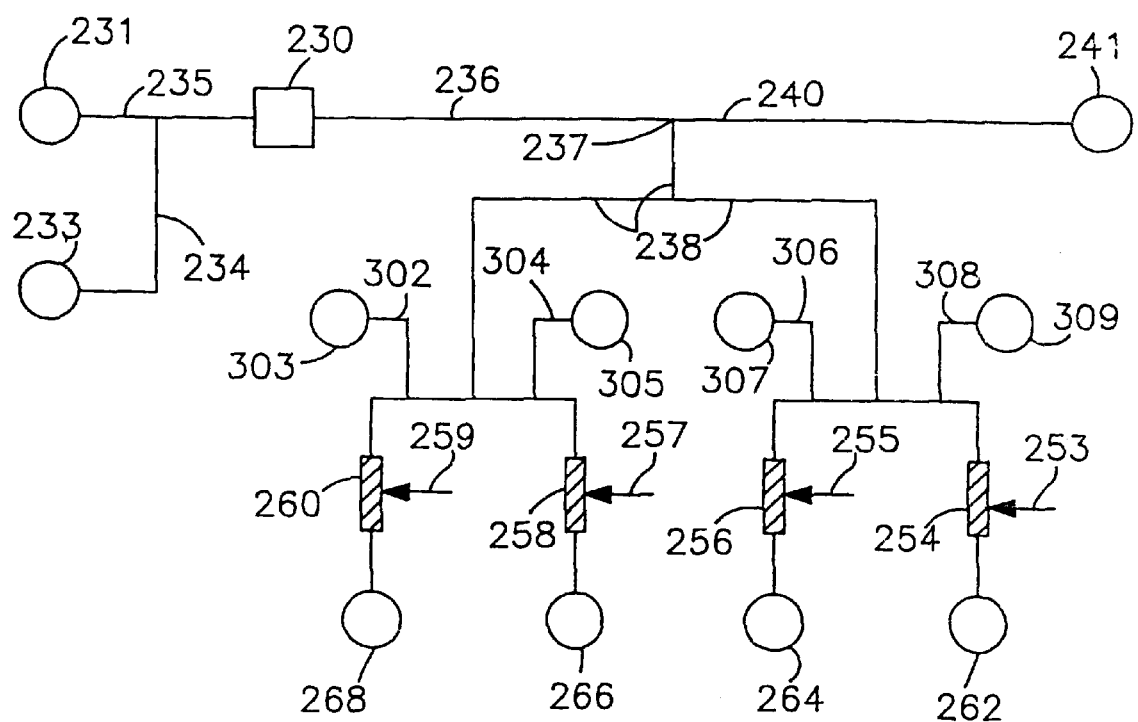
FIG. 22 is a flow diagram of an embodiment of a device according to the invention, similar to that shown in FIG. 17, respectively, and additionally having a plurality of reagent flowpaths for carrying a reagent from a reservoir directly to downstream branches of the main electrophoretic flowpath.

FIGS. 21 and 22 are flow diagrams similar to those shown in FIGS. 16 and 17, having multiple branched main electrophoretic flowpaths, each branch provided with an affinity zone. In FIG. 21 reagent flowpath 300 carries a reagent (or reagents) from a reservoir 301 to the main electrophoretic flowpath 238, where the reagent can combine with and react with one or more analytes in the enriched fraction. In this embodiment, because the reagent flowpath 300 intersects the main electrophoretic flowpath 238 at a point upstream from the first bifurcation, the reagent supplied by reservoir 301 effects a replicate treatment of all the subfractions that are treated on the downstream branches and detected in the respective affinity zones. In FIG. 22, each of the downstream branches of the main electrophoretic flowpath 238 is provided with reagent flowpath (302, 304, 306, 308) each carrying a reagent from a separate reagent reservoir (303, 305, 307, 309). Such a configuration can provide for different treatment of the subfractions, for example, providing independent stringency control of parallel hybridization zones.

For example, devices providing flowpaths as in any of FIGS. 18 through 22, or a combination of these, can be used for DNA profiling. More specifically, for example, restriction fragment polymorphism ("RFLP") analysis can be carried out by employing a plurality of different single-locus RFLP probes in reservoirs 303, 305, 307 and 309 as shown in FIG. 22. By running a large number of probes in parallel, the resulting distribution of alleles should yield a rapid and representative DNA profile, while significantly minimizing the possibility of random matches.

The subject devices may be used in a variety of applications, where one or more electric fields are applied to a medium to move entities through the medium. Representative applications include electrophoretic separation applications, nucleic acid hybridization, ligand binding, preparation applications, sequencing applications, synthesis applications, analyte identification applications, including clinical, environmental, quality control applications, and the like. Thus, depending on the particular application a variety of different fluid samples may be introduced into the subject device, where representative samples include bodily fluids, environmental fluid samples, e.g., water and the like, or other fluid samples in which the identification and/or isolation of a particular analyte is desired. Depending on the particular application, a variety of different analytes may be of interest, including drugs, toxins, naturally occurring compounds such as peptides and nucleic acids, proteins, glycoproteins, organic and inorganic ions, steroids, and the like. Of particular interest is the use of the subject devices in clinical applications, where the samples that may be analyzed include blood, urine, plasma, cerebrospinal fluid, tears, nasal or ear discharge, tissue lysate, saliva, ocular scratches, fine needle biopsies, and the like, where the sample may or may not need to be retreated, i.e., combined with a solvent to decrease viscosity, decrease ionic strength, or increase solubility or buffer to a specific pH, and the like, prior to introduction into the device. For clinical applications, analytes of interest include anions, cations, small organic molecules including metabolites of drugs or xenobiotics, peptides, proteins, glycoproteins, oligosaccharides, oligonucleotides, DNA, RNA, lipids, steroids, cholesterols, and the like.

The following examples are offered by way of illustration and not by way of limitation.

EXAMPLES

Example 1
High Efficiency Separation of Organic Analytes in an Aqueous Sample.

A card as shown in FIG. 4 is used in the separation of organic analytes in an aqueous sample as follows in conjunction with a device that provides for the application of appropriate electric fields through introduction of electrodes into each reservoir of the card and provides for a means of detecting analyte as it passes through detection region 65. In Card 50, the enrichment channel 62 comprises porous beads coated with a C-18 phase, while the reservoirs and channels, except for the waste reservoir, comprise 20 millimolar borate buffer. A 100 μl aqueous sample is injected into enrichment channel 62 through interface 66. Substantially all of the organic analyte in the sample reversibly binds to the C18 coated porous beads, while the remaining sample components flow out of enrichment channel 62 into waste reservoir 63. 10 μl of an elution buffer (90% methanol/ 10% 20 millimolar borate buffer pH 8.3) are then introduced into the enrichment channel 62 through interface 66, whereby the reversibly bound organic analyte becomes free in the elution buffer. Because of the small volume of elution buffer employed, the concentration of analyte in the volume of elution buffer as compared to the analyte concentration in the original sample is increased 100 to 1000 times. The seals over reservoirs 57 and 56 are then removed and an electric field is applied between electrodes 61 and 60, causing buffer present in 57 to move towards 56, where movement of the buffer front moves the elution plug comprising the concentrated analyte to intersection 51. A voltage gradient is then applied between electrodes 58 and 59, causing the narrow band of analyte present in the volume of elution buffer to move through separation channel 52, yielding high efficiency separation of the organic analytes.

The above experiment is also performed in a modified version of the device depicted in FIG. 4. In the modified device, in addition to reservoir 57, the device comprises an elution buffer reservoir also in fluid communication with the enrichment channel 62. In this experiment, sample is introduced into enrichment channel 62, whereby the organic analytes present in the elution buffer reversibly bind to the C18 phase coated beads present in the enrichment channel. An electric field is applied between an electrode present in the elution buffer reservoir and electrode 60 for a limited period of time sufficient to cause 10 μl of elution buffer to migrate through the enrichment channel and release any reversibly bound organic analyte. After the elution buffer has moved into the enrichment channel, a voltage gradient is then applied between electrodes 61 and 60, resulting in the movement of buffer from 57 to 56, which carries the defined volume of organic analyte comprising elution buffer to intersection 51, as described above.

Example 2
Sample Enrichment Employing Paramagnetic Beads for Enrichment Within an Integrated Microfluidic Device.

Figure 23:
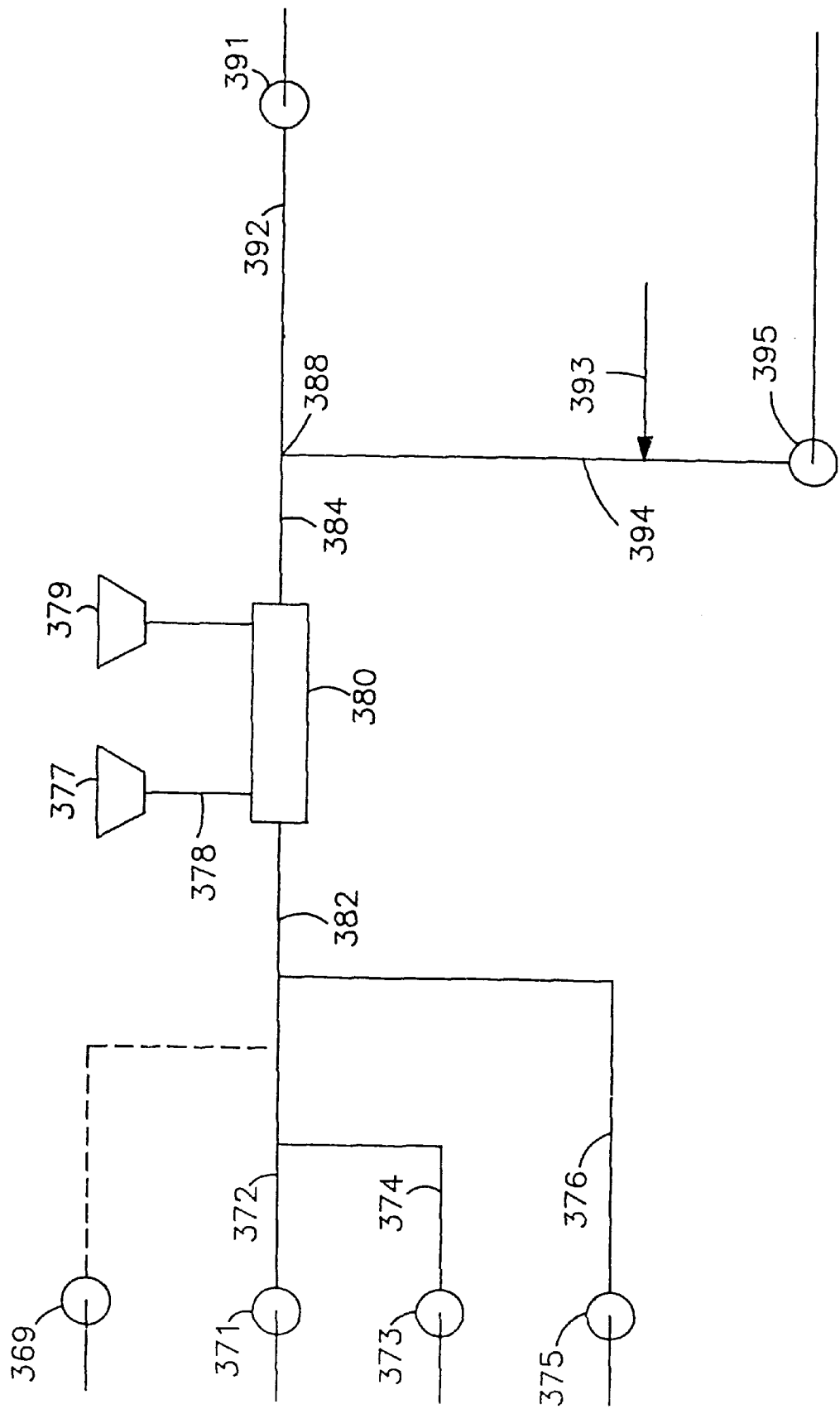
FIG. 23 is a flow diagram of an embodiment of a device according to the invention, in which the enrichment medium includes coated magnetic beads.

Experimental protocols based on biomagnetic separation methods are provided as embodiments of the current invention. In a microfluidic device configured generally as illustrated in FIG. 23, and described with reference thereto, a crude sample composed of a particular target is treated using magnetic beads, coated with an affinity medium, to capture a target having a binding affinity for the specific affinity medium. Such magnetic beads are marketed, for example, by Dynal, Inc. New York, under the name Dynabeads®. Dynabeads are superparamagnetic, monodispersed polystyrene microspheres coated with antibodies or other binding moieties that selectively bind to a target, which may be or include cells, genes, bacteria, or other biomolecules. The target-Dynabead complex is then isolated using a magnet. The resulting biomagnetic separation procedure is simple, rapid and reliable, whereby the Dynabeads serve as a generic enrichment medium for isolating specific targets from complex heterogeneous biological mixtures. Such magnetic enrichment media may be employed according to the invention in a wide variety of applications involving cell biology, molecular biology, HLA tissue typing, and microbiology, for example. Two illustrative examples are provided here, specifically, methods for DNA purification and cell isolation.

First, the microchannel-based device is generally described, and then the method of employing Dynal beads for biomagnetic separation is generally described.

The integrated microfluidic device, as shown by way of example in FIG. 23, includes a main electrophoretic flowpath 394 coupled to an enrichment channel, 382 which includes a solid phase extraction (SPE) chamber 380, and which is connected to downstream waste reservoir 391. The main electrophoretic flowpath, which consists of an enriched-sample detection region 393 and fluid outlet reservoir 395, joins the secondary electrophoretic flowpath 384 at a T intersection 388. In this configuration, sample handling is achieved electrokinetically by controlling the electric potential across the appropriate electrodes placed within the inlet reservoirs for the wash 373 and elution 375 buffers and outlet reservoirs 391 and 395.

The Dynabeads and then the sample of interest are introduced into the device through injection inlet ports 379 and 377, respectively. Within the enrichment chamber, the heterogeneous suspension of sample and Dynabeads specific for a given target incubate allowing the Dynabeads to bind the target by specific absorption to the particular capture moieties on the surface of the beads. Immobilization of the target-bead complex to the side of enrichment chamber 380 is achieved magnetically. This is possible manually by placing a rare earth permanent magnet adjacent to the enrichment chamber. In another embodiment of the invention, an automated protocol employing electromagnetic means is used to control the applied magnetic field imposed on the SPE chamber.

Upon completion of the magnetic immobilization step, a wash medium contained within wash buffer reservoir 373 can be moved via pathway 374 into and through enrichment channel 380. During sample rinsing, the waste fluid passes out from the enrichment chamber 380 by way of the electrophoretic flow path 384, then past the T intersection 388 and away through the discharge outlet 392 to waste reservoir 391. Thus, the supernatant from the wash steps is removed from the system without having to pass the waste through the main electrophoretic channel 394. This embodiment of the invention affords an advantageous means for isolating and enriching the target biomolecule from a crude sample without first contaminating the detection region 393.

Example 3
DNA Purification from Whole Blood.

An experimental method employing an electrophoretic microdevice as schematically represented in FIG. 23 is provided in which Dynal® biomagnetic beads are used as an enrichment medium for extracting and purifying genomic DNA from whole blood. The source of blood may be a small dried forensic sample on a slide (e.g., on the order of a nanogram), an aliquot of freshly drawn arterial blood (as small as 10 µl) or bone marrow (approximately 5 µl). A protocol amenable to rapid DNA isolation and elution will be provided for the purpose of demonstrating an automated procedure for treating whole blood on-board the device of FIG. 23 so as to yield aliquots of DNA for amplification and analysis or for direct analysis without amplification. The process includes the following steps:

1. reagent and sample loading;
2. cell lysis/DNA capture;
3. repetitive DNA washes; and
4) DNA elution.

Each of these steps will now be discussed in more detail.

For this embodiment in which commercially packaged reagents are being used, loading of the biomagnetic separation media, lysis solution and sample is achieved by means of specially designed injection ports to accommodate differences in the reagents and sample. The Dynal DIRECT™ reagents, which include the lysis solution and magnetic beads, are first injected directly into the solid phase extraction chamber 380 via manual injection port 379, followed by manual injection of the blood sample into the SPE chamber via the injection port 377. Alternatively, other commercial reagents may be used where the nuclei lysis solution and beads are not packaged together as a kit but are instead supplied separately. In this case, a lysis solution can be electrokinetically loaded into the SPE chamber 380 from the inlet reservoir 371. Magnetic beads, supplied for example by Japan Synthetic Rubber, are next loaded either from the injection port 379 or electrokinetically from inlet reservoir 369. For the latter approach, the beads are confined to the chamber by electromagnetic capture, mechanical means (e.g., membrane, mesh screen, or agarose gel plug) placed just downstream of the SPE chamber in flowpath 384, or both. Once the chamber is filled with beads and lysis solution, the DNA sample is added via the injection port 377, or electrokinetically via a sample inlet reservoir provided with an electrode pair with an electrode downstream from the chamber.

Within the enrichment chamber, the blood sample, lysis solution and Dynabeads are allowed to incubate for five minutes during which the cells are lysed. Released nucleic acids can then absorb to the capture moieties immobilized on the surface of the microparticles to form a DNA-bead complex. To enhance cell lysis, mixing can be achieved by, for example, arranging the supply channels so that the streams of beads, sample, and lysis solution merge. Mixing can be enhanced electrokinetically by judicious control of the applied electric field. By periodically reversing the polarity of the electrodes placed in the inlet and outlet reservoirs 371 and 391, respectively, it is possible to electrokinetically move the blood-lysis buffer mixture in an oscillatory manner within the SPE chamber. To increase further the mechanical shear applied to the cells, aperture-like structures can be molded into the SPE chamber housing.

Following the magnetic isolation and capture of the DNA-bead complex at the side of the SPE chamber, rinsing is achieved by electrokinetic transport of the wash buffer solution contained in reservoir 373 through the chamber and out to the waste reservoir 391. After this 45 second rinse, the beads are resuspended into solution by releasing the magnetic field and then allowed to incubate for one minute in the wash buffer. Following the same protocol, rinsing is repeated two more times, allowing the cell lysate and supernatant from each of the wash steps to be removed from the system without having to pass the waste, including PCR inhibitors, through the main electrophoretic channel 394.

The final step of the purification process is DNA elution. Again, the capture beads with bound DNA are immobilized electromagnetically before the elution buffer is electrokinetically transported from reservoir 373 into the SPE chamber. To obtain quantitative elution, precise manipulation of electrode potentials is necessary, not to allow the buffer to pass through the chamber and thus prematurely wash away the purified DNA. Alternatively, a plug of elution buffer may be moved into the chamber by employing an injection cross (not shown in FIG. 23) as described in D. Benvegnu et al. U.S. patent application Ser. No. 08/878,447, filed Jun. 18, 1997. With the elution buffer in the SPE chamber, the beads are resuspended by releasing the magnetic field and then allowed to incubate in the elution buffer for two minutes allowing for finite DNA desorption kinetics. Upon completion of DNA elution, the beads are immobilized electromagnetically in the SP chamber and the purified DNA is electrokinetically injected as a plug into the main electrophoretic channel 394 for analysis. The detection region 395 can represent an elaborate microfluidic system (not shown in FIG. 23) which may be comprised of a plurality of microchannels for restriction enzyme digestion, blot hybridizations, including Southern and slot/dot blots, electrophoretic fragment sizing, and quantitative PCR analysis, among others. These embodiments of the invention will not, however, be discussed further in this example.

In summary, the above protocol allows for isolation of PCR-ready aliquots of purified DNA in less than ten minutes and without user intervention once the crude sample is introduced to the microfluidic device. Other advantages of the method include the minute amount of reagents that are consumed in a given experiment, in addition to not requiring more labor intensive precipitation or centrifugation steps. ADD others.

Example 4
Cell Enrichment Employing Immunomagnetic Isolation.

An experimental protocol where Dynal® biomagnetic beads are used as an enrichment medium for isolating cell targets is provided. The procedure is similar to that described above for DNA purification. As in example 3, the target is selectively captured by beads coated with specific binding moieties immobilized on the surface of the paramagnetic microparticles. Dynabeads are available prepared in various forms, as follows:

1. precoated with affinity purified monoclonal antibodies to many human cell markers, including T cells, T cell subsets, B cells, monocytes, stem cells, myeloid cells, leukocytes and HLA Class II positive cells;
2. coated with secondary antibodies to mouse, rat, or rabbit immunoglobulins for the isolation of rodent B cells, T cells and T cell subsets;
3. in uncoated or tosylactivated form for custom coating with any given biomolecule; or
4. in streptavidin-coated form for use with biotinylated antibodies.

In a microfluidic device configured generally as illustrated in FIG. 23, a heterogeneous suspension of cells is treated employing electrokinetic and magnetic manipulation methods to prepare purified aliquots of cells for further processing and analysis. Biomagnetic separation is possible manually or in an automated format employing electromagnetic control of the magnetic field imposed on the SPE chamber. The following four step protocol is provided as a representative embodiment of the invention.

1. loading of target cells and reagents, including biomagnetic separation media: load the solution of magnetic beads into SPE chamber 380, either directly via injection port 379, or electrokinetically from the inlet reservoir 371 containing solution of Dynal beads specific to a given target; or add sample directly to SPE chamber filled with solution of Dynabeads by means of sample injection port 377.
2. cell capture employing Dynabeads capable of binding specific target:
   allow sample and beads to incubate for 2.5 minutes within the SPE chamber, enhance adsorption by employing an electrokinetic mixing step, target cells bind to Dynabeads to form target-bead complex.
3. target cell wash by immobilizing the bead-target cell complex:
   electromagnetically immobilize capture beads that contain the bound target, rinse with wash buffer solution by electrokinetic manipulation:
   remove supernatant by controlling electrode potentials so as to pass wash buffer from inlet reservoir 373 through the SP chamber to waste outlet 391,
   stop the flow after 45 seconds and resuspend target-bead complex into solution by releasing magnetic field,
   incubate the target-bead complex in wash buffer for one minute,
   repeat above wash steps two more times.
4. target cell elution employing Dynal's DETACHaBEAD™ reagents:
   immobilize capture beads electromagnetically, load the DETACHaBEAD™ solution into SP chamber 380:
   electrokinetically move the Dynal antibody-based reagent from the elution buffer reservoir 373 by manipulation of electrode potentials to avoid allowing the elution buffer to pass through the chamber, or, alternatively, an injection cross (not shown in FIG. 22) can be used to inject a plug of elution buffer into the SP chamber,
   resuspend beads by releasing magnetic field,
   incubate suspended beads in elution buffer for two minutes to allow for finite desorption kinetics,
   upon completion of target elution, immobilize beads electromagnetically
   isolated target cells can be electrokinetically transported from the SPE chamber into the main electrophoretic channel for further treatment and analysis.

Cell separations employing microfluidic devices and methods provide a cost-effective alternative to conventional flow cytometry techniques. In addition, when combined with biomagnetic separation technology, microfluidic approaches enable cell enrichment and detection that yield increased sensitivity and reduced background noise. Microfluidic-based magnetic isolation methods subject the target substances to minimal stress, and can accordingly leave cells intact and viable, ready for direct use in reverse transcription coupled with polymerase chain reaction amplification (RT-PCR). Microfluidic-based methods employ no phenol extractions, ethanol precipitations, or centrifugations, and employ few toxic reagents. Separations are provided without the use of expensive equipment and are highly scalable.

Example 5
Tools for Cost Effective Disease Management

As gene therapies move from the bench to the bedside, therapeutics and diagnostics will become more intimately interlinked. Consequently, monitoring the efficacy of DNA-based pharmaceuticals using bioinstruments at the bedside will become crucial to insuring the success of these treatments. More specifically, a microfluidic-based device for integrating cell collection and isolation processes with emerging molecular methods for DNA amplification and detection hold great promise for addressing this market need. Thus by combining methods as described in this application (particularly examples 3 and 4), it is possible to have in one analytical instrument the capability of cost-efficient disease prognosis and monitoring for helping the physician evaluate the appropriateness of a given genetic therapy. Such effective disease management strategies, in addition to other pharmacogenetic approaches, have the potential for widespread use as the post-genomic era rapidly approaches.

For the purpose of illustrating this embodiment of the invention, a system for managing blood-based diseases will be presented.

For background purposes, inherited blood disorders are the most common genetic diseases affecting humans. The World Health Organization estimates that about 5% of the world's population are carriers of different types of hemoglobin disorders and that about 300,000 new cases are diagnosed each year. Sickle cell anemia and, β-thallasemia are the two most common hemoglobinopathies that may be treated using gene therapies.

Of particular interest in treating the hemoglobinopathies, as well as monitoring the progress of their treatment, is the collection and isolation of hematopoietic stem cells. Employing the microfluidic device as shown in FIG. 22, when combined with the use of Dynal reagents for human hematopoietic progenitor cell selection as described in Example 4, a rapid and simple-to-use method for achieving the desired stem cell isolation is possible. For example, 1 ml of Dynabeads M-450 CD34 will isolate approximately $8 \times 10^7$ cells. 100 μl (one unit) of DETACHaBEAD CD34 is used to detach $4 \times 10^7$ (100 μl) Dynabeads M-450 CD34. Cells isolated with this Progenitor Cell Selection System are pure (95% from bone marrow, 90% from peripheral and cord blood) and phenotypically unaltered. On the same device, DNA analysis, including gene expression monitoring, is possible employing molecular genetic methods once the stem cells are isolated and then lysed. Thus, microfluidic-based bioanalytical devices and methods, as described in this embodiment of the invention, should prove to be invaluable tools for disease management at this emerging molecular medicine and diagnostics interface.

Example 6
Solid-phase Isolation and Enrichment

Solid phase extraction (SP) of a particular target from a heterogeneous mixture is achieved in the following embodiment of the invention by employing the selective surface properties of target-specific microparticles and mechanical means for retention of the beads within the SP chamber. Although biomagnetic separation methods are currently attractive because commercial reagents are readily available for a wide variety of bioresearch applications, other non-magnetic microfluidic-based approaches are possible for achieving comparable separations. In similar embodiments to those provided above, solid phase enrichment in a microfluidic format is presented. Beads with target-specific binding moieties can be retained within the enrichment chamber utilizing mechanical means, including filtration membranes or mesh screens. In addition, an agarose gel may be injected (from the waste reservoir 391 prior to the experiment) into channel 384 at the outlet of the enrichment chamber 380 to prevent the beads from escaping, yet allowing the wash and elution buffers to pass through the highly porous media. Thus, each of the embodiments described in Example 2 for target isolation and purification from complex mixtures may be achieved, at least conceptually, without requiring the use of magnetic fields.

Example 7

In this example affinity-binding capture and release is employed to collect and then release and separate biological entities of interest in a sample.

Here the biological entity is bound to one member of an affinity binding pair, and is captured in an enrichment zone by affinity binding with the other member on a solid support. The enriched captures biological entity is then released, for example, by competitive displacement of the binding pair by a binding pair member having a higher affinity.

In particular, for example, the biological entity of interest may be DNA. Generally, the method proceed as follows. One member of an affinity binding pair is attached at the 5' end of a selected oligonucleotide sequencing primer, which may be about 10–30 bases in length, usually about 15–25 bases, or about 20 bases in length, to form a functionalized primer. The DNA of interest is combined with the functionalized primer in the presence of nucleotides under conditions favoring extension of the primer to form DNAs, complementary to the DNA of interest, and amplifying specific portions of the DNA. A dye terminator can be employed in the reaction to provide a chromophore for fluorescence detection of the amplified DNA portions. Each resulting amplified DNA has a functional group at the 5' end of each strand, and carries the chromophore. This sequencing reaction can be conducted outside the device, and the amplified DNA can be introduced to the enrichment channel by way of an inlet port; or the reaction can be conducted on the device itself.

The other member of the binding pair is then attached to a solid surface, so that when the functionalized DNAs are brought into contact with the solid surface under conditions favoring affinity binding of the binding pair members, the DNAs are captured on the solid phase. According to the invention, the solid phase may be particles or beads, which can themselves be manipulated into, within, and out from the channels or chambers of the device.

Release of the captured DNAs is then effected by introducing a binding pair member that has a significantly higher affinity, with the result that it displaces either the binding pair member on the functionalized DNAs, or the binding pair member on the solid support. This results in freeing the DNAs of interest, which can then flow out from the enrichment channel to a separation channel.

Any of a variety of affinity binding pairs may be used. For example, an avidin-biotin system may be employed. Avidin is attached to the solid support, and a modified biotin, having a significantly lower affinity for avidin than unmodified biotin, is attached to the oligonucleotide primer. Amplification is carried out, and then the amplified DNAs are captured in the device by binding of the modified biotin to the avidin on the solid support. Then release of the DNAs is effected by introducing biotin into the enrichment channel to displace the modified biotin, and the DNAs are moved out from the enrichment channel.

In an illustrative example, the functionalized oligonucleotide primer is-the M13/pUC forward 23-base sequencing primer, with dethiobiotin attached at the 5' end, to form:

dethiobiotin-5'-CCCAG TCACG ACGTT GTAAA ACG-3' (SEQ ID NO:1)

Figure 26:
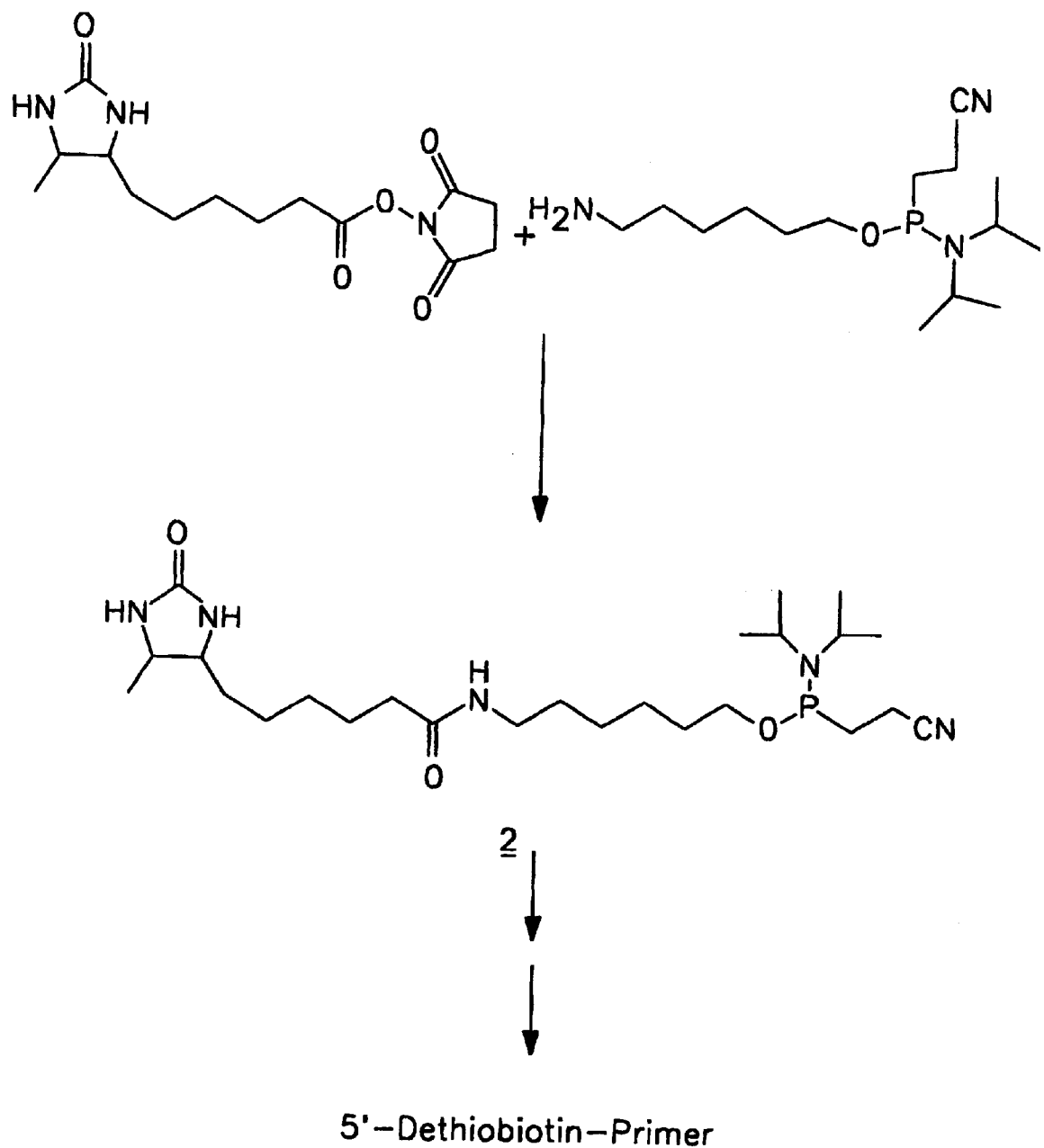
FIG. 26 is a reaction scheme showing synthesis of the 5-dethiobiotin-primer construct as described in Example 7.

A general method of attaching dethiobiotin molecule to an oligonucleotide is shown in FIG. 26. Briefly, N-hydroxysuccinimidodedliobiotin (K. Ilofinann et al. (1982), *Biochemistry*, Vol. 21, page 978) (0.1 mMole) was reacted with 5' Amino-modifier C6 T (Glen Research; 0.1 Mole) as shown FIG. 26, to form dethiobiotin. To prepare the dethiobiotin-functionalized primer, the dethiobiotin was introduced by using dethiobiotin amidite ([2] in FIG. 26) in the last step of the oligonucleotide synthesis on a DNA synthesizer. After cleavage from the solid support and removal of the base protecting groups the dethiobiotin conjugated primers were used in the sequencing reactions.

Figure 24:
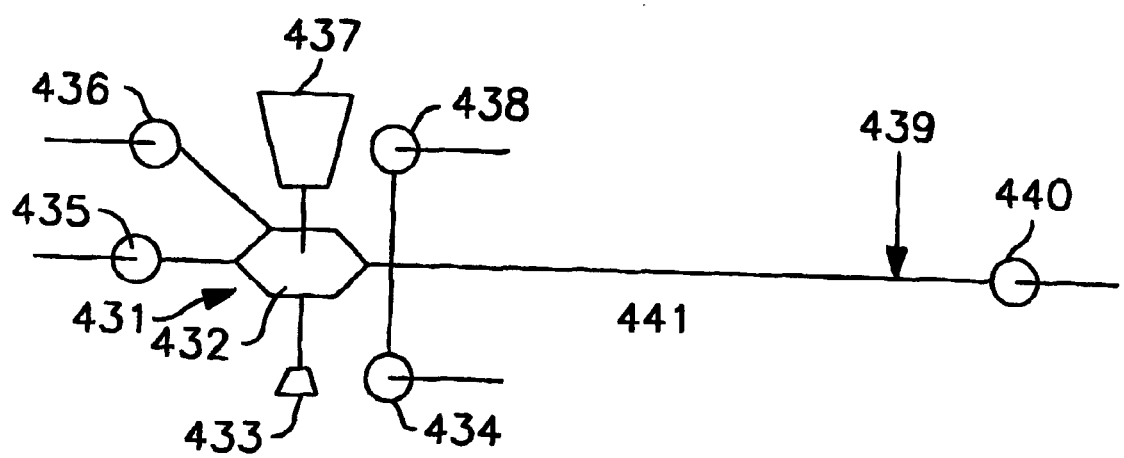
FIGS. 24 and 25 are flow diagrams showing embodiments of a device according to the invention, as may be used in the DNA capture method described in Example 7.
Figure 25:
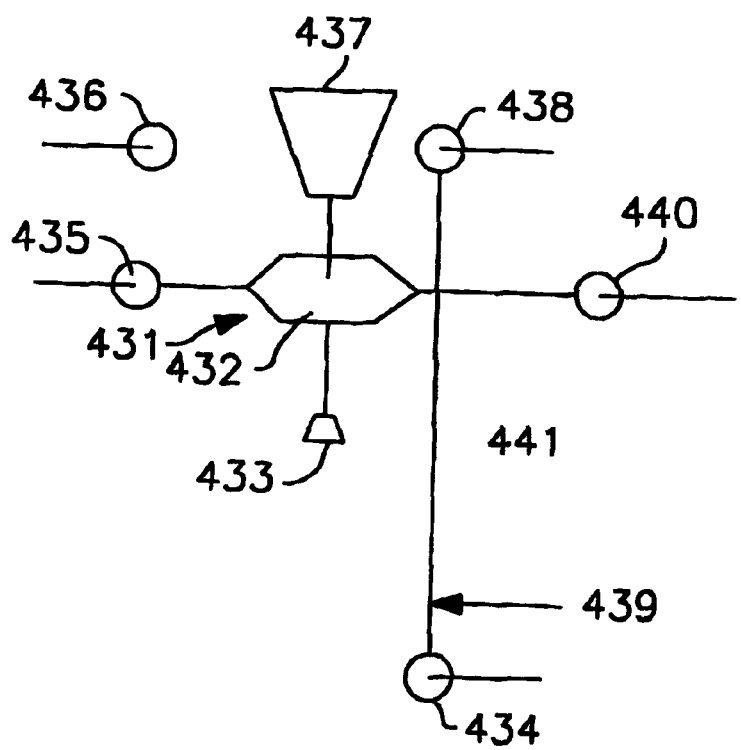

Following amplification the amplified DNAs include a dethiobiotin functional group at the end of each strand of DNA. Referring now to FIG. 24, the DNA sequencing products in the sample can be added to sample inlet port 437. A filter or membrane material may be located at the bottom of the port to restrict access of particulate matter from sample enrichment medium 432 that is confined within sample enrichment channel 431. Preferably, the channels making up the device are located within a plane of the device, while the sample is introduced into the device from outside the plane of the device (for example, from above), and the treated sample and/or wastes may leave the enrichment zone from any dimension. In the embodiments shown in FIGS. 24 and 25 the treated sample leaves the enrichment zone through the waste fluid outlet 433 below the plane of the device. All the reservoirs 435, 436, 434, 438, 440 contain buffer, while reservoir 435 additionally contains biotin in an amount in the range 10 $\mu$Molar to 1000 $\mu$Molar. The flow through the enrichment zone can be controlled by application of a pressure gradient between the inlet 437 and the waste fluid outlet 433. Alternatively, the sample can be migrated through the enrichment zone by application of an electric field between the sample inlet and a waste fluid reservoir.

Beads or particles are coated with the protein carboxyavidin, which has a strong affinity for dethiobiotin, and therefore will selectively enrich that component of the sample. The enrichment zone can be rinsed by application of an electrical potential between reservoirs 436 and either 433 or 438. Following capture of the DNA sample, biotin located in reservoir 435 is moved through the enrichment zone by application of an electric field between reservoirs 435 and 438. Biotin has significantly greater affinity for the carboxyevidin molecule than does dethiobiotin (Kd=$10^{-15}$ M for biotin, vs. $10^{-11}$ M for dethiobiotin), and consequently it displaces the DNA of interest from the beads in the enrichment zone. Injection of the released DNAs into the main electrophoresis channel 441 is performed by switching the electric field for about 5 seconds to reservoirs 435 and 440. This causes a portion of the released DNA to migrate into the separation media within separation channel 441. Changing the electric field between 434 and 440 results in separation of the DNA in the main electrophoresis channel. The separation is detected at an optical detector 439.

In an alternative embodiment, differing in the arrangement of channels downstream from the enrichment channel, DNA is moved toward reservoir 440 until a representative sampling is available at the inlet to the main separation channel 441. Injection of the DNA is accomplished by simply switching the electric field to reservoirs 438 and 434 to perform the separation of DNA for detection at 439.

It is evident from the above results and discussion that convenient, integrated microchannel electrophoretic devices are disclosed which provide for significant advantages over currently available CE and MCE devices. Because the subject devices comprise microchannels as electrophoretic flowpaths, they provide for all of the benefits of CE and MCE devices, including rapid run times, the ability to use small sample volumes, high separation efficiency, and the like. Since the subject integrated devices comprise an enrichment channel, they can be employed for the analysis of complex sample matrices comprising analyte concentrations in the femtomolar to nanomolar range. However, because of the particular positional relationship of the enrichment channel and the main electrophoretic flowpath, the shortcomings of on-line configurations, such as band broadening and the like, do not occur in the subject devices. As the subject devices are integrated and compact, they are easy to handle and can be readily used with automated devices. Finally, with the appropriate selection of materials, the devices can be fabricated so as to be disposable. Because of their versatility and the sensitivity they provide, the subject devices are suitable for use in a wide variety of applications, including clinical electrophoretic assays.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

contacting in the enrichment region bound entities with the second binding member of the affinity binding pair, which is bound to at least one solid support to capture at least a part of the bound entities to form a captured nucleic acid portion, washing the captured nucleic acid portion to direct the waste portion and the nucleic acid portion excluding the captured nucleic acid portion through said discharge outlet and away from the working region, releasing the captured nucleic acid portion by competitive displacement of the first binding member bound to the captured nucleic acid portion with a competitive displacing member having a higher affinity for the second binding member than the first binding member to yield a purified nucleic acid portion, and transporting the purified nucleic acid portion to the working region, whereby the purified nucleic acid portion is processed or analyzed or processed and analyzed in the working region.

2. The method according to claim 1 wherein the combining step is performed after the introducing step.

3. The method according to claim 1 wherein the introducing step is performed after the combining step.

4. The method according to claim 1 further comprising the step of amplifying the purified nucleic acid portion in the working region.

5. The method according to claim 4 wherein the amplifying step includes the step of performing PCR amplification on the purified nucleic acid portion.

6. The method according to claim 1 further comprising the step of nucleic acid sequencing the purified nucleic acid portion in the working region.

---

---

What is claimed is:

1. A method for nucleic acid sample clean-up using a substrate having a surface and an enrichment microchannel, a main electrophoretic flowpath and a discharge outlet, formed in the substrate, said enrichment microchannel comprising an enrichment region and said main electrophoretic flowpath comprising a working region, said enrichment microchannel being in fluid transfer relationship with said main electrophoretic flowpath, and an affinity binding pair having complementary first and second binding members, said first binding member comprising a label, said method comprising the steps of:

introducing a nucleic acid mixture having a nucleic acid portion and a waste portion into the enrichment microchannel, combining the first binding member of the affinity binding pair with the nucleic acid portion of at least some of the nucleic acid mixture to form a labeled nucleic acid portion of bound entities between nucleic acid molecules of said nucleic acid portion and said labeled first binding member, 7. The method according to claim 6 wherein the nucleic acid sequencing step includes the step of dideoxy enzymatic chain-termination sequencing the purified nucleic acid portion.

8. The method according to claim 1 wherein the first binding member includes modified biotin molecule having a lower affinity than biotin to the second binding member.

9. The method according to claim 8 wherein the modified biotin molecule is dethiobiotin.

10. The method according to claim 8 wherein the modified biotin molecule is a dethiobiotin derivative.

11. The method according to claim 1 wherein the second binding member includes an avidin-based protein.

12. The method according to claim 1 wherein the at least one solid support includes a plurality of magnetic bodies.

13. The method according to claim 1 wherein the at least one solid support includes a plurality of paramagnetic bodies.

14. The method according to claim 1 wherein the competitive displacing member includes a biotin molecule.

15. The method according to claim 1 wherein the nucleic acid portion of the nucleic acid mixture includes a DNA template and a sequencing primer.

16. The method according to claim 1 wherein the nucleic acid portion of the nucleic acid mixture includes a terminal dideoxynucleotide analog.

17. The method according to claim 1 wherein the nucleic acid portion of the nucleic acid mixture includes deoxynucleotide.

18. The method according to claim 1 wherein the first binding member includes dethiobiotin and wherein said second binding member includes an avidin-based protein and the competitive displacing member includes a biotin molecule, further comprising the step of performing PCR amplification on the purified nucleic acid portion in the working region.

* * * * *

SEQUENCE LISTING

<160> NUMBER OF SEQ ID NOS: 1

<210> SEQ ID NO 1
<211> LENGTH: 23
<212> TYPE: DNA
<213> ORGANISM: Oligonucleotide

<400> SEQUENCE: 1
cccagtcacg acgttgtaaa acg                    23